US008119400B2

(12) United States Patent
Monahan et al.

(10) Patent No.: US 8,119,400 B2
(45) Date of Patent: Feb. 21, 2012

(54) METHODS OF INHIBITING SMOOTH MUSCLE CELL MIGRATION AND PROLIFERATION

(75) Inventors: Thomas S. Monahan, Brookline, MA (US); Frank W. LoGerfo, Cambridge, MA (US); Nicholas D. Andersen, Boston, MA (US)

(73) Assignee: Beth Isreal Deaconess Medical Center, Inc., Boston, MA (US)

( * ) Notice: Subject to any disclaimer, the term of this patent is extended or adjusted under 35 U.S.C. 154(b) by 185 days.

(21) Appl. No.: 11/890,318

(22) Filed: Aug. 3, 2007

(65) Prior Publication Data

US 2008/0299654 A1 Dec. 4, 2008

Related U.S. Application Data

(63) Continuation of application No. PCT/US2006/004823, filed on Feb. 9, 2006.

(60) Provisional application No. 60/651,336, filed on Feb. 9, 2005.

(51) Int. Cl.
*C12N 15/85* (2006.01)
*C07H 21/04* (2006.01)
*C07H 21/02* (2006.01)
*A61K 48/00* (2006.01)

(52) U.S. Cl. ............... 435/325; 536/23.1; 536/24.31; 536/24.33; 536/24.5; 514/44

(58) Field of Classification Search .................. None
See application file for complete search history.

(56) References Cited

U.S. PATENT DOCUMENTS

| | | | |
|---|---|---|---|
| 4,987,071 A | 1/1991 | Cech et al. | |
| 5,427,916 A | 6/1995 | Gewirtz et al. | |
| 5,849,902 A | 12/1998 | Arrow et al. | |
| 6,683,057 B1 | 1/2004 | Koch et al. | |
| 6,730,313 B2 | 5/2004 | Helmus et al. | |
| 2002/0173478 A1 | 11/2002 | Gewirtz | |
| 2004/0018176 A1 | 1/2004 | Tolentino et al. | |
| 2004/0126784 A1 | 7/2004 | Hitoshi et al. | |

FOREIGN PATENT DOCUMENTS

| | | |
|---|---|---|
| WO | WO 00/50062 A2 | 8/2000 |
| WO | WO 2004/033620 A2 | 4/2004 |
| WO | WO 2006/086681 A2 | 8/2006 |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Abid, M.R., et al., "Forkhead Transcription Factors Inhibit Vascular Smooth Muscle Cell Proliferation and Neointimal Hyperplasia," *J. Biol. Chem.*, 280: 29864-29873 (2005).
Andersen, N.D., et al., "Comparison of Gene Silencing in Human Vascular Cells Using Small Interfering RNAs," *J. Am. Coll. Surg.*, 204(3): 399-408 (2007).
Arbuzova, A., et al., "Cross-Talk Unfolded: MARCKS Proteins," *Biochem. J.*, 362: 1-12 (2002).
Boehm, M. and E.G. Nabel, "The Cell Cycle and Cardiovascular Diseases," *Prog. in Cell Cycle Res.* 5: 19-30 (2003).
Bustin, S.A., "Quantification of mRNA Using Real-Time Reverse Transcription PCR (RT-PCR): Trends and Problems," *J. Mol. Endocrinol.*, 29: 23-39 (2004).
Castro, C., et al., "Distinct Regulation of Mitogen-Activated Protein Kinases and p27$^{Kip1}$ in Smooth Muscle Cells from Different Vascular Beds," *J. Biol. Chem.*, 278: 4482-4490 (2003).
Conte, M.S., et al., "Genetic Interventions for Vein Bypass Graft Disease: A Review," *J. Vasc. Surg.*, 36(5): 1040-1052 (2002).
Davies, M.G., and Hagen, P.-O., "Pathophysiology of Vein Graft Failure: A Review," *Eur. J Vasc. Endovasc. Surg*, 9: 7-18 (1995).
Eichholtz, T., et al., "A Myristoylated Pseudosubstrate Peptide, A Novel Protein Kinase C Inhibitor," *J. Biol. Chem.*, 268: 1982-1986 (1993).
Feinberg, A.P. and Vogelstein, B., "A Technique for Radiolabeling DNA Restriction Endonuclease Fragments to High Specific Activity," *Anal. Biochem.*, 132: 6-13 (1983).
Gallagher, S., et al., "Immunoblotting and Immunodetection." In *Current Protocols in Molecular Biology*, F. Ausubel, et al., eds. (NJ: John Wiley & Sons, Inc.) vol. 2, Chapter 10, pp. 10.8.1-10.8.24 (1998).
Hammann, C., et al., "Length Variation of Helix III in a Hammerhead Ribozyme and its Influence on Cleavage Activity," *Antisense and Nucleic Acid Drug Dev.*, 9: 25-31 (1999).
Itoh, H., et al., "Differential Effects of Protein Kinase C on Human Vascular Smooth Muscle Cell Proliferation and Migration," *Am. J. Physiol. Heart Cir. Physiol.*, 281: H359-H370 (2001).
Izzard, T.D., et al., "Mechanisms Underlying Maintenance of Smooth Muscle Cell Quiescence in Rat Aorta: Role of the Cyclin Dependent Kinases and Their Inhibitors," *Cardiovasc. Res.* 53(1): 242-252 (2002). Kalish, J.A., et al., "Temporal Genomics of Vein Bypass Grafting Through Oligonucleotide Microarray Analysis," *J. Vasc. Surg.*, 39: 645-654 (2004).
Lange, A. et al., "20-Hydroxyeicosatetraenoic Acid-Induced Vasoconstriction and Inhibition of Potassium Current in Cerebral Vascular Smooth Muscle is Dependent on Activation of Protein Kinase C," *J. Biol. Chem.*, 272: 27345-27352 (1997).
Li, J., et al., "Myristoylated Alanine-rich C Kinase Substrate-mediated Neurotensin Release via Protein Kinase C-δ Downstream of the Rho/ROK Pathway," *J. Biol. Chem.*, 280: 8351-8357 (2005).
Li, Y., et al., "Essential Role of the Low Density Lipoprotein Receptor-related Protein in Vascular Smooth Muscle Cell Migration," *FEBS Lett.*, 555: 346-350 (2003).

(Continued)

*Primary Examiner* — Amy Bowman
(74) *Attorney, Agent, or Firm* — Hamilton, Brook, Smith & Reynolds, P.C.

(57) ABSTRACT

In particular embodiments, the present invention provides methods of inhibiting smooth muscle cell responses and methods of treating or preventing vascular proliferative disease caused by smooth muscle cell migration and proliferation. More specifically, smooth muscle cell responses are inhibited by introducing an agent into smooth muscle cells, wherein the agent inhibits an activity of one or more members of the myristoylated alanine-rich C kinase substrate (MARCKS) family of proteins. The invention also provides methods of inhibiting expression of one or more genes encoding a member of the MARCKS family of proteins in a cell.

18 Claims, 26 Drawing Sheets

OTHER PUBLICATIONS

LoGerfo, F.W., et al., "A Clinical Technique for Prevention of Spasm and Preservation of Endothelium in Saphenous Vein Grafts," *Arch. Surg.*, 119(10): 1212-1214 (1984).

Mann, M.J. and Conte, M.S., "Transcription Factor Decoys for the Prevention of Vein Bypass Graft Failure," *Am. J. Cardiovasc. Drugs*, 3(2): 79-85.

Mann, M.J., et al., "Ex-vivo Gene Therapy of Human Vascular Bypass Grafts with E2F Decoy: the PREVENT Single-centre, Randomised, Controlled Trial," *Lancet*, 9189: 1493-1498 (1999).

Mann, M.J. and V.J. Dzau, "Therapeutic Applications of Transcription Factor Decoy Oligonucleotides," *J. Clin. Invest.*, 106: 1071-1075 (2000).

Mann, M.J., et al. "Pressure-Mediated Oligonucleotide Transfection of Rat and Human Cardiovascular Tissues," *Proc. Natl. Acad. Sci. USA*, 96: 6411-6416 (1999).

McManus, M.T. and P.A. Sharp, "Gene Silencing in Mammals by Small Interfering RNAs," *Nat. Rev. Genet.*, 3(10): 737-747 (2002).

McNamara, R.K., et al., "Effect of Reduced Myristoylated Alanine-rich C Kinase Substrate Expression on Hippocampal Mossy Fiber Development and Spatial Learning in Mutant Mice: Transgenic Rescue and Interactions with Gene Background," *Proc. Natl. Acad. Sci. USA*, 95: 14517-14522 (1998).

Rigby, P.W.J., et al., "Labeling Deoxyribonucleic Acid to High Specific Activity in Vitro by Nick Translation with DNA Polymerase I," *J. Mol. Biol.*, 113: 237-251 (1977).

"Extraction, Purification, and Analysis of Messenger RNA from Eukaryotic Cells." In *Molecular Cloning: A Laboratory Manual*, J. Sambrook, et al., eds. (NY: Cold Spring Harbor Laboratory Press), $2^{nd}$ Ed., Chapter 7, pp. 7.3-7.53 (1989).

Shintani, T., et al., "Intraoperative Transfection of Vein Grafts with the NFκB Decoy in a Canine Aortocoronary Bypass Model: A Strategy to Attenuate Intimal Hyperplasia," *Ann. Thorac. Surg.*, 74(4): 1132-1137 (2002).

Song, E., et al., "RNA Interference Targeting Fas Protects Mice from Fulminant Hepatitis," *Nature Med.*, 9(3): 347-351 (2003).

Stein, C.A. and Cheng, Y.-C., "Antisense Oligonucleotides as Therapeutic Agents—Is the Bullet Really Magical?" *Science*, 261: 1004-1012 (1993).

Voytik-Harbin, S.L., et al., "Application and Evaluation of the Alamarblue Assay for Cell Growth and Survival of Fibroblasts," *In Vitro Cell. Dev. Biol.*, 34(3): 239-246 (1998).

Werner, M. and Uhlenbeck, O.C., "The Effect of Base Mismatches in the Substrate Recognition Helices of Hammerhead Ribozymes on Binding and Catalysis," *Nucl. Acids Res.*, 23: 2092-2096 (1995).

Willis, D.J., et al. "Temporal Gene Expression Following Prosthetic Arterial Grafting," *J. Surg. Res.*, 120: 27-36 (2004).

Wu, M., et al., "Neural Tube Defects and Abnormal Brain Development in F52-Deficient Mice," *Proc. Natl. Acad.. Sci. USA*, 93: 2110-2115 (1996).

Zhao, Y., et al., "Role of MARCKS in Regulating Endothelial Cell Proliferation," *Am. J. Physiol. Cell Physiol.*, 279: C1611-C1620 (2000).

http://www.cosmobio.co.jp/product2/product_SCB_20040428/SCB_siRNA%20list%20(2004.11.10).pdf.

* cited by examiner

HCASMCs

HCAECs

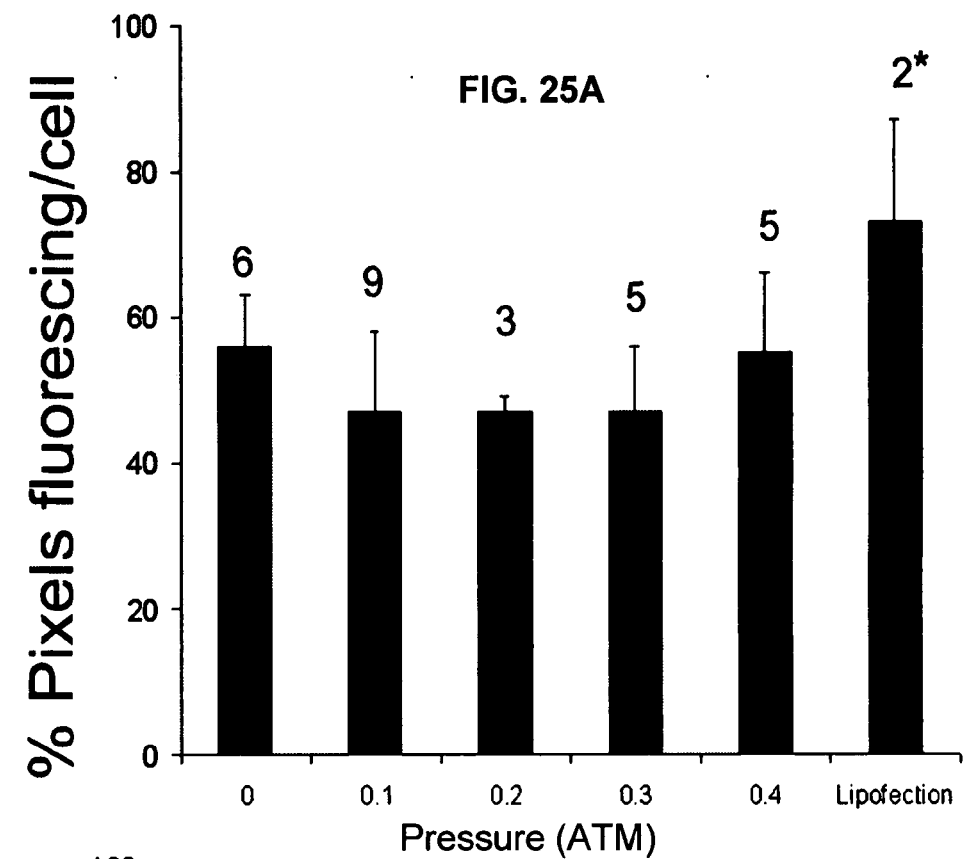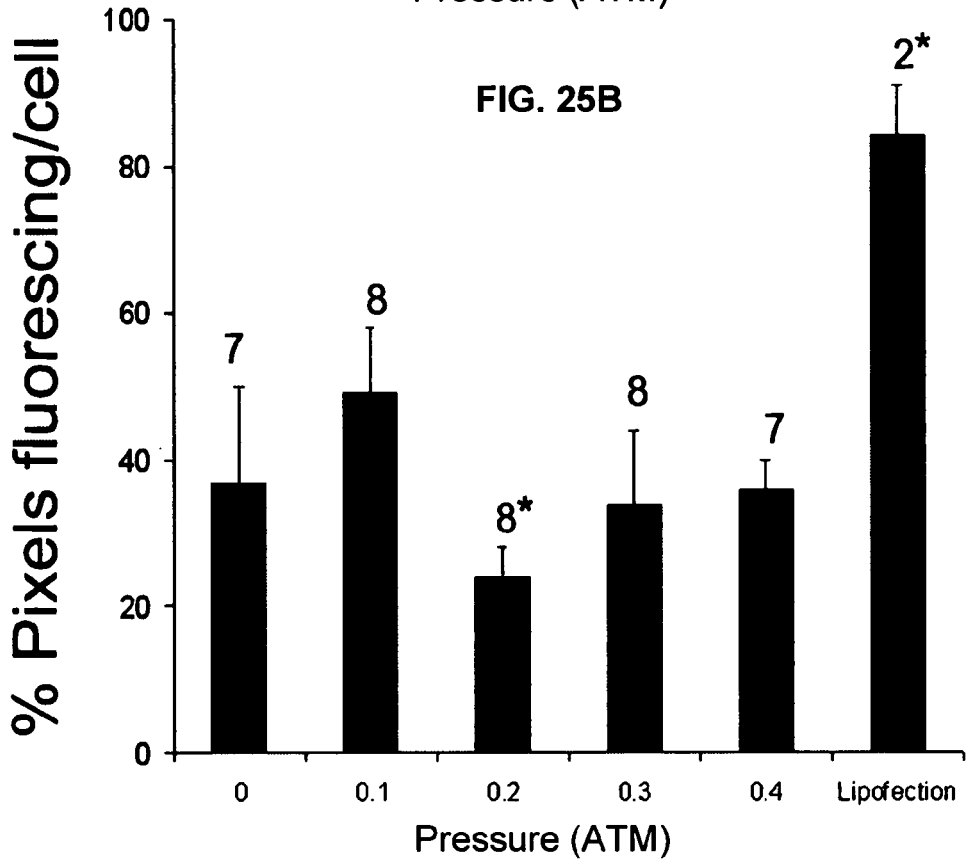

Fluorescence Intensity

METHODS OF INHIBITING SMOOTH MUSCLE CELL MIGRATION AND PROLIFERATION

RELATED APPLICATIONS

This application is a continuation of International Application No. PCT/US2006/004823, which designated the United States and was filed on Feb. 9, 2006, published in English, which claims the benefit of U.S. Provisional Application No. 60/651,336, filed on Feb. 9, 2005. The entire teachings of the above applications are incorporated herein by reference.

GOVERNMENT SUPPORT

The invention was supported, in whole or in part, by grants HL21796-21 and T32 HL07734 from the National Institutes of Health. The Government has certain rights in the invention.

BACKGROUND OF THE INVENTION

Cardiovascular disease is a leading cause of death in industrialized countries. Interventional surgical procedures, such as autogenous bypass operations and coronary angioplasty, often fail due to restenosis, a pathological condition wherein rapid re-occlusion of blood vessels at sites of vascular injury is elicited by manipulations performed during surgery. Restenosis arises due to the onset and maintenance of intimal hyperplasia, a process characterized by excessive cellular proliferation of vascular smooth muscle cells (VSMCs). Vascular injury caused by surgical procedures induces biological responses that stimulate VSMCs to migrate to the intima of an injured blood vessel. Intimal hyperplasia, characterized by the subsequent proliferation of VSMCs at the intima, leads to deposition of excessive extracellular matrix and ultimately, vascular occlusion.

To enhance the efficacy of vascular reconstructive procedures and prevent vein graft and arterial graft failure, it will be necessary to develop therapies for inhibiting migration and/or proliferation of VSMCs at sites of vascular injury. Drugs with anti-proliferative properties, such as rapamycin and paclitaxel, have shown promise in inhibiting VSMC migration and proliferation during clinical trials. (see, e.g., Boehm, M. and Nabel, E. G. (2003) *Progress in Cell Cycle Research* 5:19-30). Presently, there is an urgent need to identify and develop additional agents that are capable of reducing VSMC hyperplasia. Such agents could be applied to the prevention and treatment of restenosis and other vascular proliferative diseases.

SUMMARY OF THE INVENTION

The present invention encompasses methods of inhibiting a cellular response in smooth muscle cells and methods of inhibiting expression of genes encoding members of the myristoylated alanine-rich C kinase substrate (MARCKS) family of proteins. Activation of protein kinase C (PKC) plays a vital role in VSMC migration and proliferation. Proteins of the MARCKS-family are major cellular substrates of PKC activity, and expression of at least one member of this family, the MARCKS protein, is upregulated in a canine model of vascular grafting (see, e.g., Arbuzova et al. (2002) *Biochem. J* 362:1-12 and Willis, D J et al. (2004) *Journal of Surgical Research* 120:27-36). As such, MARCKS-family proteins present promising molecular targets for therapies directed to treating vascular proliferative diseases.

In one embodiment, the invention provides a method for inhibiting a smooth muscle cell response by providing smooth muscle cells with an agent that inhibits an activity of one or more members of the MARCKS family of proteins. As defined herein, a member of the MARCKS family of proteins includes any of the known family members, e.g, MARCKS protein and MacMARCKS protein—also known as MARCKS-related protein, MRP, MLP, MARCKS-Like 1 and F52—as well as any yet unidentified members of this family. Nucleotide and amino acid sequences of MARCKS and MacMARCKS are shown in Table 1.

TABLE 1

MacMARCKS and MARCKS cDNA and protein sequences.

| Name | Sequence | SEQ ID NO. |
|---|---|---|
| MacMARCKS cDNA | GGCATTCTGGCGCGGAGCGGAGCGGCGGCGGGCGCAGCTAGCGG GTCGGCCGCGGAGCGGAGGTGCAGCTCGGCTTCCCCCGGCACCC CTCCCACTCGGGCGCCAGCCCCACCCCTCAGCCGGCCGGGCCGA CCACGCCGTACTATCCCCTGCGGCGCGAGCCCGGGGCGGCTCCA AGCGCCCCCAGCAGACCCCCATCATGGGCAGCCAGAGCTCCAA GGCTCCCCGGGGCGACGTGACCGCCGAGGAGGCAGCAGGCGCTT CCCCCGCGAAGGCCAACGGCCAGGAGAATGGCCACGTGAAAAGC AATGGAGACTTATCCCCCAAGGGTGAAGGGGAGTCGCCCCCTGT GAACGAACAGATGAGGCAGCCGGGGCCACTGGCGATGCCATCG AGCCAGCACCCACTAGCCAGGGTGCTGAGGCCAAGGGGGAGGTC CCCCCCAAGGAGACCCCCAAGAAGAAGAAGAAATTCTCTTTCAA GAAGCCTTTCAAATTGAGCGGCCTGTCCTTCAAGAGAAATCGGA AGGAGGGTGGGGGTGATTCTTCTGCCTCCTCACCCACAGAGGAA GAGCAGGAGCAGGGGGAGATCGGTGCCTGCAGCGACGAGGGCAC TGCTCAGGAAGGGAAGGCCGCAGCCACCCCTGAGAGCCAGGAAC CCCAGGCCAAGGGGGCAGAGGCTAGTGCAGCCTCAGAAGAAGAG GCAGGGCCCCAGGCTACAGAGCCATCCACTCCCTCGGGGCCGGA GAGTGGCCCTACACCAGCCAGCGCTGAGCAGAATGAGTAGCTAG GTAGGGGCAGGTGGGTGATCTCTAAGCTGCAAAAACTGTGCTGT CCTTGTGAGGTCACTGCCTGGACCTGGTGCCCTGGCTGCCTTCC TGTGCCCAGAAAGGAAGGGGCTATTGCCTCCTCCCAGCCACGTT CCGTTTCCTCCTCTCCCTCCTGTGGATTCTCCCATCAGCCATCT GGTTCTCCTCTTAAGGCCAGTTGAAGATGGTCCCTTACAGCTTC CCAAGTTAGGTTAGTGATGTGAAATGCTCCTGTCCCTGGCCCTA CCTCCTTCCCTGTCCCCACCCCTGCATAAGGCAGTTGTTGGTTT | 1 |

TABLE 1-continued

MacMARCKS and MARCKS cDNA and protein sequences.

| Name | Sequence | SEQ ID NO. |
|---|---|---|
| | TCTTCCCCAATTCTTTTCCAAGTAGGTTTTGTTTACCCTACTCC<br>CCAAATCCCTGAGCCAGAAGTGGGGTGCTTATACTCCCAAACCT<br>TGAGTGTCCAGCCTTCCCCTGTTGTTTTTAGTCTCTTGTGCTGT<br>GCCTAGTGGCACCTGGGCTGGGGAGGACACTGCCCCGTCTAGGT<br>TTTTATAAATGTCTTACTCAAGTTCAAACCTCCAGCCTGTGAAT<br>CAACTGTGTCTCTTTTTTGACTTGGTAAGCAAGTATTAGGCTTT<br>GGGGTGGGGGAGGTCTGTAATGTGAAACAACTTCTTGTCTTTT<br>TTTCTCCCACTGTTGTAAATAACTTTTAATGGCCAAACCCCAGA<br>TTTGTACTTTTTTTTTTTTCTAACTGCTAAAACCATTCTCTTC<br>CACCTGGTTTTACTGTAACATTTGGAAAAGGAATAAATGTCGTC<br>CCTTTAAAAAAAAAAAAAAAAAAAAAAAAAAAAAAAAAAA | |
| MacMARCKS Protein | MGSQSSKAPRGDVTAEEAAGASPAKANGQENGHVKSNGDLSPKG<br>EGESPPVNGTDEAAGATGDAIEPAPTSQGAEAKGEVPPKETPKK<br>KKKFSFKKPFKLSGLSFKRNRKEGGGDSSASSPTEEEQEQGEIG<br>ACSDEGTAQEGKAAATPESQEPQAKGAEASAASEEEAGPQATEP<br>STPSGPESGPTPASAEQNE | 2 |
| MARCKS cDNA | TCGACTTTTCCACCCTTTTTCCCTCCCTCCTGTGCTGCTGCTTT<br>TTGATCTCTTCGACTAAAATTTTTTTATCCGGAGTGTATTTAAT<br>CGGTTCTGTTCTGTCCTCTCCACCACCCCCACCCCCTCCCTCC<br>GGTGTGTGTGCCGCTGCCGCTGTTGCCGCCGCCGCTGCTGCTGC<br>TGCTCGCCCCGTCGTTACACCAACCCGAGGCTCTTTGTTTCCCC<br>TCTTGGATCTGTTGAGTTTCTTTGTTGAAGAAGCCAGCATGGGT<br>GCCCAGTTCTCCAAGACCGCAGCGAAGGGAGAAGCCGCCGCGGA<br>GAGGCCTGGGGAGGCGGCTGTGGCCTCGTCGCCTTCCAAAGCGA<br>ACGGACAGGAGAATGGCCACGTGAAGGTAAACGGCGACGCTTCG<br>CCCGCGGCCGCCGAGTCGGGCGCCAAGGAGGAGCTGCAGGCCAA<br>CGGCAGCCCCCGGCCGCCGACAAGGAGGAGCCCGCGGCCGCCG<br>GGAGCGGGGCGGCGTCGCCCTCCGCGGCCGAGAAAGGTGAGCCG<br>GCCGCCGCCGCTGCCCCCGAGGCCGGGGCCAGCCCGGTAGAGAA<br>GGAGGCCCCGCGGAAGGCGAGGCTGCCGAGCCCGGCTCGCCCA<br>CGGCCGCGGAGGGAGAGGCCGCGTCGGCCGCCTCCTCGACTTCT<br>TCGCCCAAGGCCGAGGACGGGGCCACGCCCTCGCCCAGCAACGA<br>GACCCCGAAAAAAAAAAAGAAGCGCTTTTCCTTCAAGAAGTCTT<br>TCAAGCTGAGCGGCTTCTCCTTCAAGAAGAACAAGAAGGAGGCT<br>GGGAGAAGGCGGTGAGGCTGAGGCGCCCGCTGCCGAAGGCGGCAA<br>GGACGAGGCCGCCGGGGGCGCAGCTGCGGCCGCCGCCGAGGCGG<br>GCGCGGCCTCCGGGGAGCAGGCAGCGGCGCCGGGCGAGGAGGCG<br>GCAGCGGGCGAGGAGGGGCGGCGGGTGGCGACCCGCAGGAGGC<br>CAAGCCCCAGGAGGCCGCTGTCGCGCCAGAGAAGCCGCCCGCCA<br>GCGACGAGACCAAGGCCGCCGAGGAGCCCAGCAAGGTGGAGGAG<br>AAAAAGGCCGAGGAGGCCGGGGCCAGCGCCGCCGCCTGCGAGGC<br>CCCCTCCGCCGCCGGGCCCGGCGCGCCCCCGGAGCAGGAGGCAG<br>CCCCCCGCGGAGGAGCCCGCGGCCGCCGCAGCCTCGTCAGCCTGC<br>GCAGCCCCCTCACAGGAGGCCCAGCCCGAGTGCAGTCCAGAAGC<br>CCCCCCAGCGGAGGCGGCAGAGTAAAAGAGCAAGCTTTTGTGAG<br>ATAATCGAAGAACTTTTCTCCCCCGTTTGTTTGTTGGAGTGGTG<br>CCAGGTACTGGTTTTGGAGAACTTGTCTACAACCAGGGATTGAT<br>TTTAAAGATGTCTTTTTTTATTTTACTTTTTTTTAAGCACCAAA<br>TTTTGTTGTTTTTTTTTCTCCCCTCCCCACAGATCCCATCTCA<br>AATCATTCTGTTAACCACCATTCCAACAGGTCGAGGAGAGCTTA<br>AACACCTTCTTCCTCTGCCTTGTTTCTCTTTTATTTTTTATTTT<br>TTCGCATCAGTATTAATGTTTTTGCATACTTTGCATCTTTATTC<br>AAAAGTGTAAACTTTCTTTGTCAATCTATGGACATGCCCATATA<br>TGAAGGAGATGGGTGGGTCAAAAAGGGATATCAAATGAAGTGAT<br>AGGGGTCACAATGGGGAAATTGAAGTGGTGCATAACATTGCCAA<br>AATAGTGTGCCACTAGAAATGGTGTAAAGGCTGTCTTTTTTTT<br>TTTTTTTAAAGAAAAGTTATTACCATGTATTTTGTGAGGCAGGT<br>TTACAACACTACAAGTCTTGAGTTAAGAAGGAAAGAGGAAAAAA<br>GAAAAAACACCAATACCCAGATTTAAAAAAAAAAAACGATCAT<br>AGTCTTAGGAGTTCATTTAAACCATAGGAACTTTTCACTTATCT<br>CATGTTAGCTGTACCAGTCAGTGATTAAGTAGAACTACAAGTTG<br>TATAGGCTTTATTGTTTATTGCTGGTTTATGACCTTAATAAAGT<br>GTAATTATGTATTACCAGCAGGGTGTTTTAACTGTGACTATTG<br>TATAAAAACAAATCTTGATATCCAGAAGCACATGAAGTTTGCAA<br>CTTTCCACCCTGCCCATTTTTGTAAAACTGCAGTCATCTTGGAC<br>CTTTTAAAACACAAATTTTAAACTCAACCAAGCTGTGATAAGTG<br>GAATGGTTACTGTTTATACTGTGGTATGTTTTGATTACAGCAG<br>ATAATGCTTTCTTTTCCAGTCGTCTTTGAGAATAAAGGAAAAAA<br>AAATCTTCAGATGCAATGGTTTTGTGTAGCATCTTGTCTATCAT<br>GTTTTGTAAATACTGGAGAAGCTTTGACCAATTTGACTTAGAGA<br>TGGAATGTAACTTTGCTTACAAAAATTGCTATTAAACTCCTGCT<br>TAAGGTGTTCTAATTTTCTGTGAGCACACTAAAAGCGAAAATA<br>AATGTGAATAAAATGTAAAAAAAAAAAAAAAAAAAAAAAA | 3 |

TABLE 1-continued

MacMARCKS and MARCKS cDNA and protein sequences.

| Name | Sequence | SEQ ID NO. |
|---|---|---|
| | AAAAAAAA | |
| MARCKS Protein | MGAQFSKTAAKGEAAAERPGEAAVASSPSKANGQENGHVKVNGD ASPAAAESGAKEELQANGSAPAADKEEPAAAGSGAASPSAAEKG EPAAAAPEAGASPVEKEAPAEGEAAEPGSPTAAEGEAASAASS TSSPKAEDGATPSPSNETPKKKKKRFSFKKSFKLSGFSFKKNKK EAGEGGEAEAPAAEGGKDEAAGGAAAAAAEAGAASGEQAAAPGE EAAAGEEGAAGGDPQEAKPQEAAVAPEKPPASDETKAAEEPSKV EEKKAEEAGASAAACEAPSAAGPGAPPEQEAAPAEEPAAAAASS ACAAPSQEAQPECSPEAPPAEAAE | 4 |

As defined herein, the term "smooth muscle cell response" includes smooth muscle cell proliferation and smooth muscle cell migration. In particular, smooth muscle cells encompassed by the present invention include vascular smooth muscle cells (also referred to herein as VSMCs). In a particular embodiment, the invention is a method for inhibiting a smooth muscle cell response by contacting (e.g., transfecting or introducing) smooth muscle cells with an agent that inhibits expression of one or more genes encoding a member of the MARCKS family of proteins. In a further embodiment, the agent induces post-transcriptional silencing of one or more genes encoding a member of the MARCKS family of proteins. Suitable agents for this embodiment include siRNA molecules having sequence homology with a MARCKS-family gene transcript, wherein the RNA molecule binds to (or hybridizes to, or interacts with) portions or segments of a MARCKS-family gene transcript, thereby suppressing/inhibiting protein expression of a MARCKS family member. In another embodiment, the method comprises providing smooth muscle cells with an agent that acts as a MARCKS antagonist, thereby inhibiting MARCKS activity in these cells. In a further embodiment of the present invention, inhibition of MARCKS expression or activity results in inhibition of intimal hyperplasia, and in particular, inhibition of MARCKS activity results in the inhibition of vein graft failure.

BRIEF DESCRIPTION OF THE DRAWINGS

FIG. 25A is a bar graph showing quantitation of cell fluorescence in HCASMCs at 24 hours post-transfection with Cy5-siRNA and demonstrating that no increase in fluorescence was observed as the transfecting pressure was increased. The number of cells quantitated for each treatment is listed above each bar in the graph. * denotes P<0.05. Cell fluorescence from confocal micrographs of cells lipofected with Cy5-siRNA (Lipofection) was included for comparison.

FIG. 25B is a bar graph showing quantitation of cell fluorescence in HCAECs at 24 hours post-transfection and demonstrating that no increase in fluorescence was observed as the transfecting pressure was increased. The number of cells quantitated for each treatment is listed above each bar in the graph. * denotes P<0.05. Cell fluorescence from confocal micrographs of cells lipofected with Cy5-siRNA (Lipofection) was included for comparison.

DETAILED DESCRIPTION OF THE INVENTION

Figure 1A:
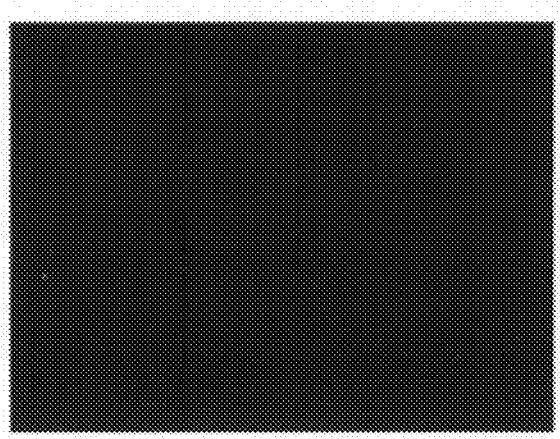
FIG. 1A is a fluorescent image of VSMCs transfected with unlabeled siRNA. Cells are shown at 40× magnification.

Methods of Inhibiting Smooth Muscle Cell Responses

Smooth muscle cell migration and proliferation are underlying causes of vascular proliferative diseases induced by interventional surgical procedures. Smooth muscle cell proliferation is known to be activated by protein kinase C (PKC) signaling pathways (Itoh, H. et al (2001) *Am. J. Physiol. Heart Circ. Physiol.* 281:H359-370, 2001). Major cellular substrates of PKC activity are members of the myristoylated alanine-rich C kinase substrate (MARCKS) family of proteins. Expression of one such family member, the MARCKS protein, is upregulated in canine vein grafts, suggesting that MARCKS may contribute to VSMC migration and proliferation (see, e.g., Willis, D J et al. (2004) *Journal of Surgical Research* 120:27-36). The present invention results from the discovery that VSMC migration and proliferation are mediated by MARCKS-family proteins, and that these cellular responses can be inhibited by interfering with the function of one or more MARCKS-family proteins, in a cell.

In certain embodiments, the invention provides methods for inhibiting a smooth muscle cell response comprising providing smooth muscle cells with an agent that interferes with an activity of one or more protein members of the MARCKS family of proteins. As used herein, "smooth muscle cells" include, but are not limited to, vascular, intestinal, airway and prostatic smooth muscle cells. In one embodiment, the invention is a method of inhibiting a cellular response of vascular smooth muscle cells (VSMCs). In a further embodiment, the VSMCs are human VSMCs, and are located in a vascular tissue, such as a vein, artery, vein graft or arterial graft.

Smooth muscle cells are known to undergo a variety of cellular responses when presented with response-inducing stimuli. As used herein, a "cellular response of smooth muscle cells" is any smooth muscle cell response including proliferation, growth, migration, differentiation, and changes in cell shape or morphology.

In one embodiment, the invention is a method of inhibiting smooth muscle cell proliferation. As used herein, "proliferation" refers to an increase in rate and/or quantity of cell divisions, leading to an elevation in cell number. Techniques for assaying cell proliferation are well known in the art. Suitable techniques for the invention include, but are not limited to, detecting an antigen which is present in proliferating cells but absent in non-proliferating cells, measuring DNA synthesis, or monitoring the reducing environment of proliferating cells. Antigenic markers for proliferating cells include PCNA and methods of measuring DNA synthesis encompass, among others, quantitation of 3H-thymidine incorporation, 5-bromodeoxyuridine (BrdU) incorporation, or Hoechst 33258 incorporation. Methods of monitoring the reducing environment of a cell include quantitation of tetrazolium salt reduction.

Smooth muscle cell proliferation can also be assessed using an alamarBlue Reduction assay, as described in Examples 2 and 7. alamarBlue is a soluble compound which gains electrons from the highly reduced environment of actively proliferating cells and emits light at a wavelength of 590 nm. Measurements of alamarBlue reduction may be made either spectrophotometrically or fluorometrically. Proliferation may therefore be monitored using either a standard spectrophotometer, a standard spectrofluorimeter, a spectrophotometric microtiter well plate reader, or spectrofluorometric microtiter well plate reader.

In another embodiment, the invention encompasses methods of inhibiting smooth muscle cell migration. As used herein, "migration" refers to the movement of a cell from one location to another. A multitude of assays for monitoring cellular migration have been developed and are well known in the art. One such assay, described in Examples 2 and 7, monitors migration of fluorescently-labeled cells across a cell-permeable membrane in response to a chemotactic stimulus.

The methods of the invention comprise, introducing into smooth muscle cells, an agent that inhibits an activity of one or more members of the MARCKS family of proteins. As defined herein, a member of the MARCKS family of proteins includes any of the known family members, as well as any yet unidentified members of this family. The MARCKS family of proteins includes two known members, e.g., the MARCKS protein and MacMARCKS protein, also known as MARCKS-related protein, MRP, MLP, MARCKS-Like 1 and F52. MARCKS and MacMARCKS are known substrates of protein kinase C (PKC) and both of these proteins possess three conserved domains—an MH2 domain of unknown function, a phosphorylation site domain containing all serine residues known to be PKC phosphorylation sites, and a highly basic domain, often referred to as the effector domain or ED (Arbuzova et al. (2002) *Biochem. J* 362:1-12).

In one embodiment, an "agent that inhibits an activity of one or more members of the MARCKS family of proteins" is any drug, organic or inorganic molecule, protein peptide that functions as an inhibitor of expression of one or more genes encoding a member of the MARCKS family of proteins. As used herein, an "inhibitor of MARCKS gene expression" either decreases or eliminates levels of one or more MARCKS-family gene products in a cell. Examples of MARCKS-family gene products include any RNA produced by transcription of a MARCKS-family gene, as well as any MARCKS-family protein.

In a further embodiment, the agent is an inhibitor of gene expression that induces post-transcriptional silencing of one or more genes encoding a member of the MARCKS family of proteins. These inhibitors can be double-stranded RNA (such as short- or small-interfering RNA or "siRNA"), antisense nucleic acids, or enzymatic RNA molecules such as ribozymes, among others. Each of these compounds can be designed to target and either destroy or induce the destruction of MARCKS mRNA, in vivo.

Expression of a MARCKS-family gene can be inhibited by inducing RNA interference ("RNAi"), a technique that is well known in the art. RNA interference (RNAi) provides a method of post-transcriptional gene regulation, and silencing RNAs (siRNA) are the active intermediates of the RNAi pathway. siRNA duplexes can be designed to contain sequence homology to individual genes. When present in a cell, siRNA duplexes are separated, and the resulting single-stranded RNAs are recognized by RNA interference silencing complexes (RISC). RISC complexes bind the separated RNA strands and are directed with near-perfect specificity by sequence homology to complementary mRNA strands. The RISC complexes then cleave the mRNA strands without disrupting the siRNA molecules, thereby allowing RISC complexes to be recycled and catalytically degrade additional mRNA strands (see, e.g., McManus M T, Sharp P A. (2002) *Nat. Rev. Genet.* 10: 737-47). In this manner, siRNAs can be said to knockdown gene expression by degrading mRNA, and knockdown levels greater than 90% have been achieved in mammalian cells using this method (see, e.g., Song E, et al. (2003) *Nat. Med.* 9: 347-51. 2003).

In one embodiment, the inhibitor of MARCKS gene expression is double-stranded RNA having homology to a MARCKS-family gene transcript. To achieve RNAi of the MARCKS gene, an isolated double-stranded RNA ("dsRNA") molecule which has at least 90%, for example 95%, 98%, 99% or 100%, sequence homology with at least a portion of a MARCKS-family gene transcript is used. dsRNA having 100% sequence homology to a portion of a MARCKS-family gene transcript, although preferred, is not required. In a further embodiment, the dsRNA molecule is a "short or small interfering RNA" or "siRNA." cDNA sequences for MARCKS and MacMARCKS gene products are provided in Table 1.

siRNA that are useful in the present methods include short double-stranded RNA from about 17 nucleotides to about 29 nucleotides in length, preferably from about 19 to about 22 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target MARCKS-family gene transcript. In a particular embodiment, the siRNA comprises a nucleic acid sequence that is 100% identical to a nucleic acid sequence contained within the target MARCKS-family gene transcript. In a further embodiment the siRNA comprises the nucleic acid sequence of SEQ ID NO. 18 and/or SEQ ID NO. 19.

As used herein, a nucleic acid sequence in an siRNA which is "substantially identical" to a target sequence contained within the target RNA is a nucleic acid sequence which is identical to the target sequence, or which differs from the target sequence by one or two nucleotides, such that the nucleic acid sequence in the siRNA can bind specifically to the target RNA. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be an RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus in one embodiment, the siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a certain embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated MARCKS-family gene products. Exemplary methods for producing and testing dsRNA or siRNA molecules are described in U.S. published patent application 2002/0173478 to Gewirtz and in U.S. published patent application 2004/0018176 to Reich et al., the entire disclosures of which are herein incorporated by reference.

Expression of a MARCKS-family gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) and generally comprise a nucleic acid sequence complementary to a contiguous nucleic acid sequence in a MARCKS-family gene transcript. Preferably, the antisense nucleic acid comprises a nucleic acid sequence which is 50-100% complementary, more preferably 75-100% complementary, and most preferably 95-100% complementary to a contiguous nucleic acid sequence in an MARCKS-family gene product. cDNA sequences for MARCKS and MacMARCKS gene products are provided in Table 1.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector. Exemplary methods for producing and testing are known to one skilled in the art; see, e.g., Stein and Cheng (1993), *Science* 261:1004 and U.S. Pat. No. 5,849,902 to Woolf et al., the entire disclosures of which are herein incorporated by reference.

Expression of a MARCKS-family gene can also be inhibited by an enzymatic nucleic acid. As used herein, an "enzymatic nucleic acid" refers to a nucleic acid comprising a substrate binding region that has complementarity to a contiguous nucleic acid sequence of a MARCKS-family gene transcript, and which is able to specifically cleave a MARCKS-family gene transcript. Preferably, the enzymatic nucleic acid substrate binding region is 50-100% complementary, more preferably 75-100% complementary, and most preferably 95-100%% complementary to a contiguous nucleic acid sequence in a MARCKS-family gene transcript. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated MARCKS gene products. Exemplary methods for producing and testing ribozymes are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are herein incorporated by reference.

Inhibition of expression of a gene encoding a protein belonging to the MARCKS-family can be assessed using any technique suitable for detecting levels of MARCKS-family gene products in cells. Techniques for determining the level of RNA transcripts are well known in the art. For example, the relative number MARCKS gene transcripts in cells can be determined by reverse transcription of MARCKS gene transcripts, followed by amplification of the reverse-transcribed products by polymerase chain reaction (RT-PCR). The levels of MARCKS gene transcripts can be quantified in comparison with an internal standard, for example, levels of mRNA from a "housekeeping" gene present in the same sample. A suitable "housekeeping" gene for use as an internal standard includes myosin or glyceraldehyde-3-phosphate dehydrogenase (G3PDH or GAPDH). The methods for quantitative RT-PCR and variations thereof are within the skill in the art.

In another example, total cellular. RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given MARCKS-family gene product can be produced from the nucleic acid sequences provided in Table 1. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are herein incorporated by reference.

For example, the nucleic acid probe can be labeled with, e.g., a radionuclide such as $^3$H, $^{32}$P, $^{33}$P, $^{14}$C, or $^{35}$S; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977), *J. Mol. Biol* 113:237-251 or by the random priming method of Fienberg et al. (1983), *Anal. Biochem.* 132:6-13, the entire disclosures of which are herein incorporated by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of MARCKS gene transcript levels. Alternatively, MARCKS gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate the dTTP analogue 5-(N-(N-biotinyl-epsilon-aminocaproyl)-3-aminoallyl)deoxyuridine triphosphate into the probe molecule. The biotinylated probe oligonucleotide can be detected by reaction with biotin-binding proteins such as avidin, streptavidin, or anti-biotin antibodies coupled with fluorescent dyes or enzymes which produce color reactions.

In addition to RT-PCR, Northern blotting and other RNA blotting hybridization techniques, determining the levels of RNA transcripts can be accomplished by the technique of in situ hybridization. This technique requires fewer cells than the Northern blotting technique, and involves depositing whole cells onto a microscope cover slip and probing the nucleic acid content of the cell with a solution containing radioactive or otherwise labeled cDNA, or RNA probes. The practice of the in situ hybridization technique is described in more detail in U.S. Pat. No. 5,427,916, the entire disclosure of which is incorporated herein by reference. Suitable probes for in situ hybridization of a MARCKS gene product can be produced, as described above, from the nucleic acid sequences provided in Table 1.

Other techniques for measuring MARCKS-family gene transcripts are also within the skill in the art, and include various techniques for measuring rates of RNA transcription and degradation.

In addition to techniques for measuring levels of RNA transcripts, techniques for assaying protein levels in cells are well known in the art. Such techniques include, but are not limited to, Western blotting, immunohistochemistry (IHC) and immunoassays (e.g., ELISA). A standard technique for assaying protein levels in a cellular extract is the Western blotting technique, described in Current Protocols in Molecular Biology, F. Ausubel et al., eds., Vol. 2, John Wiley and Sons, Inc., 1998, Chapter 10, the entire disclosure of which is incorporated herein by reference. For example, cell extracts containing total cellular protein can be prepared by homogenizing cells in the presence of protein extraction buffer. The proteins are then separated by gel electrophoresis on polyacrylamide gels according to standard techniques, and transferred from the gel to nitrocellulose filters. Detection and quantification of a specific protein is accomplished using appropriately labeled antibodies that recognize and bind to the protein of interest. Detection of a MARCKS-family protein in vascular smooth muscle cell extracts by Western blotting is described in Examples 3, 7 and 8 below.

In another embodiment of the invention, an "agent that inhibits an activity of one or more members of the MARCKS family of proteins" is any drug, molecule or protein that decreases or inhibits (including competitive inhibition) one or more biological activities of one or more members of the MARCKS-family of proteins. An example of such an agent is an antagonist of a MARCKS-family protein. Such antagonists of the present invention include, but are not limited to, antibodies (e.g., monoclonal antibodies, polyclonal antibodies, humanized antibodies, chimeric antibodies, human antibodies, antibody conjugates), antibody fragments (e.g., Fab fragments, Fab' fragments, F(ab')2 fragments), peptide inhibitors, small organic molecules, fragments or mutants of a MARCKS-family protein and protein kinase C (PKC) inhibitors.

In a particular embodiment, the antagonist is the PKC inhibitor, 20-28 (Calbiochem, La Jolla, Calif.), represented by the amino acid sequence Myr-Phe-Ala-Arg-Lys-Gly-Ala-Leu-Arg-Gln, wherein Myr is a myristoyl group lipid modification at the amino terminus of the molecule. The PKC inhibitor 20-28 is a peptide PKC pseudosubstrate that has been shown to inhibit MARCKS phosphorylation in vivo as described in Eichholtz, T. et al. (1993) *J. Biol. Chem.* 268: 1982-1986, the entire teachings of which are incorporated herein by reference.

The MARCKS-family inhibitory agents of the present invention can be delivered to smooth muscle cells using any technique suitable for introducing molecules or compounds into eukaryotic cells. For example, agents that inhibit MARCKS activity can be delivered into cells by transfection. Techniques for transfecting molecules into cells are well known in the art. Examples of transfection methods include, but are not limited to, transfection by direct delivery, such as direct injection of the nucleic acid into the nucleus or pronucleus of a cell or electroporation; carrier-mediated methods such as liposomal transfer, transfer mediated by lipophilic materials, receptor mediated nucleic acid delivery, calcium phosphate coprecipitation, or DEAE-dextran treatment; and transfection mediated by viral vectors. In a particular embodiment, a MARCKS-family inhibitory agent is transfected into a cell by lipofection. In another embodiment, a MARCKS-family inhibitory agent is transfected into a cell using pressure (e.g., nondistending pressure, distending pressure). In yet another embodiment, a MARCKS-family inhibitory agent is transfected into a cell by soaking the cell in a solution containing siRNA.

In the present methods, a MARCKS inhibitory agent can be administered to the subject either as a naked molecule (nucleic acid, protein, or other), in combination with a delivery reagent, or as a recombinant plasmid or viral vector comprising sequences which express the MARCKS inhibitory compound. Suitable delivery reagents include calcium phosphate, DEAE-dextran, liposomal reagents such as DOTAP and DOSPER (Roche Applied Science), the FuGENE reagent (Roche Applied Science), the Mirus Transit TKO lipophilic reagent, lipofectin, lipofectamine, cellfecti, or polycations (e.g., polylysine). In a particular embodiment, the multi-component lipid reagent, FuGENE, is used to deliver siRNA into smooth muscle cells, as described in Example 1.

Methods of transfecting VSMCs from vascular tissues and grafts are known in the art. Such techniques are described in Examples 4 and 5 below and in the disclosures of Mann, M J, et al. (1999) *Lancet* 9189:1493-8 and Mann, M J. Dzau, V J. (2000) *J. Clin. Invest.* 106:1071-1075, the entire teachings of which are herein incorporated by reference.

Methods of Treating or Preventing Vascular Proliferative Diseases

Vascular reconstructive surgical procedures, such as vein grafting, often fail because they are followed by the rapid onset of proliferative disease upon completion of the surgery. These diseases are elicited by migration and proliferation of VSMCs at sites of vascular damage, a process known as intimal hyperplasia. The present invention is based upon the discovery that inhibiting MARCKS activity in VSMCs decreases both migration and proliferation of VSMCs in culture, as described in Examples 2 and 7 herein.

In one embodiment, the invention is a method of treating or preventing vascular proliferative disease in a mammalian subject by administering an agent that inhibits an activity of one or more members of the MARCKS family of proteins. In a particular embodiment, the method is directed to treating a human subject. In a further embodiment, the invention encompasses the use of an agent that inhibits an activity of one or more members of the MARCKS family of proteins for the treatment or prevention of vascular proliferative disease in a subject. In another embodiment, the invention encompasses the use of an agent that inhibits an activity of one or more members of the MARCKS family of proteins for the manufacture of a medicament for the treatment or prevention of vascular proliferative disease in a subject.

As used herein, "vascular proliferative diseases" are any diseases or conditions that result from pathological migration and/or proliferation of vascular smooth muscle cells. Examples of vascular proliferative diseases suitable for such treatment include intimal hyperplasia, atherosclerosis, restenosis, and vascular graft hyperplasia. In a particular embodiment, the method is directed to preventing intimal hyperplasia in a subject. In another embodiment, the method is directed to preventing vein graft failure in a subject. Several methods for administering and delivering agents to sites of vascular damage are described in U.S. Pat. No. 6,730,313 to Helmus et al., the entire teachings of which are herein incorporated by reference.

Methods of Inhibiting MARCKS Gene Expression in a Cell

The present invention also encompasses methods of inhibiting expression of one or more genes encoding a member of the MARCKS family of proteins in a cell, comprising delivering an agent into the cell that mediates post-transcriptional silencing of a MARCKS-family gene. Suitable cells for these methods include any eukaryotic cells that express one or more MARCKS-family proteins. In one embodiment, the cell is a vascular cell (e.g., a vascular smooth muscle cell, a vascular endothelial cell). In a further embodiment, the vascular cell is present in a vascular tissue, such as a vein, artery, vein graft or arterial graft. Appropriate agents for mediating post-transcriptional silencing of the MARCKS-family genes are discussed above and include, but are not limited to, double-stranded RNA (such as short- or small-interfering RNA or "siRNA"), antisense nucleic acids, or enzymatic RNA molecules such as ribozymes. In a particular embodiment, the inhibitor of gene expression is siRNA having homology with a MARCKS-family gene transcript. In a further embodiment, the siRNA comprises the nucleic acid sequence of SEQ ID NO. 18 and/or SEQ ID NO. 19.

Methods of detecting post-transcriptional silencing of expression of a MARCKS-family gene can be assessed using any technique suitable for detecting the levels of MARCKS-family gene products in cells. Common examples include RT-PCR (e.g., quantitative RT-PCR or qRT-PCR), Northern Blot analysis, immunohistochemistry (IHC) and Western Blot analysis, each of which is described herein.

Methods of delivering an agent that promotes post-transcriptional silencing of a MARCKS-family gene in a cell includes any technique suitable for introducing molecules or compounds into eukaryotic cells. In one embodiment, the agent is introduced into cells by transfection, as discussed above. In a further embodiment, the agent is transfected using the multi-component lipid reagent, FuGENE, described in Example 1. In a related embodiment, transfection of the agent is performed as described in Examples 4, 5, 7, 8 or 9.

Example 1

Transfection of Vascular Smooth Muscle Cells (VSMCs) with siRNA

Materials and Methods

In this study, VSMCs were transfected with Cy3-labeled siRNA (Dharmacon Research, Inc., Lafayette, Colo.). Cells were grown to near confluence on a specially created slide-mounted tissue culture chamber (Lab-Tek Chamber Slide System, Nunc, Inc., Naperville, Ill.). This system provided a surface for the cells to attach to with a removable surrounding aseptic chamber. When cells neared confluence, they were transfected with 100 nM of Cy3-labeled siRNA (Dharmacon Research, Inc.) mixed with the lipid transfection reagent FuGENE (Roche Applied Science, Indianapolis, Ind.) in a ratio of 3 µl FuGENE to 1 µg siRNA in serum and antibiotic free media. The cells were incubated in this reaction mixture for 24 hours. After 24 hours of transfection, the chamber component of the slide apparatus was removed and the cells were fixed with Vectashield mounting medium (Vector, Burlingame, Calif.). The slides were visualized with a fluorescent microscope using an excitation wavelength of 550 nm and an emission wavelength of 570 nm.

To quantitate transfection efficiency, fluorescence-activated cell sorting (FACS) analysis was performed on cells transfected with 250 nM siRNA that was either labeled with Cy3 or was unlabeled (Dharmacon Research, Inc.). VSMCs were grown to near confluence in tissue culture flasks. The cells were then transfected with the RNA-FuGENE transfection mixture for 24 hours as described above. The cells were harvested and the entire contents of each flask were resuspended in 500 µl of FACS buffer, supplemented with 0.02% paraformaldehyde. The cells were washed twice, run on a FACS machine and separated by the appropriate filter for Cy3. Transfection efficiency was determined by performing FACS and observing the shift in fluorescence intensity of the transfected cells.

Results

Figure 1B:
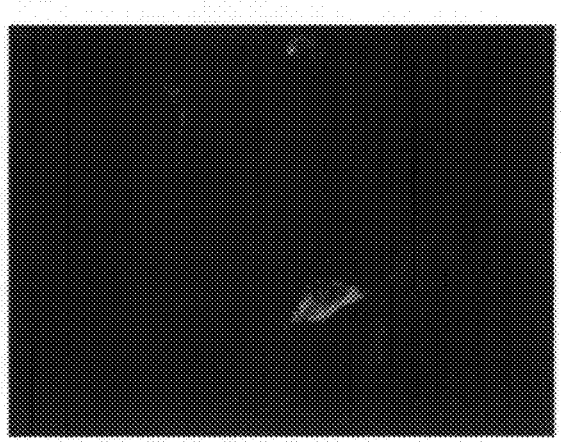
FIG. 1B is a fluorescent image of VSMCs transfected with Cy3-labeled siRNA. Cells are shown at 40× magnification. Perinuclear cytoplasmic granules are visible in these cells, indicating the cells have been transfected successfully.
Figure 2:
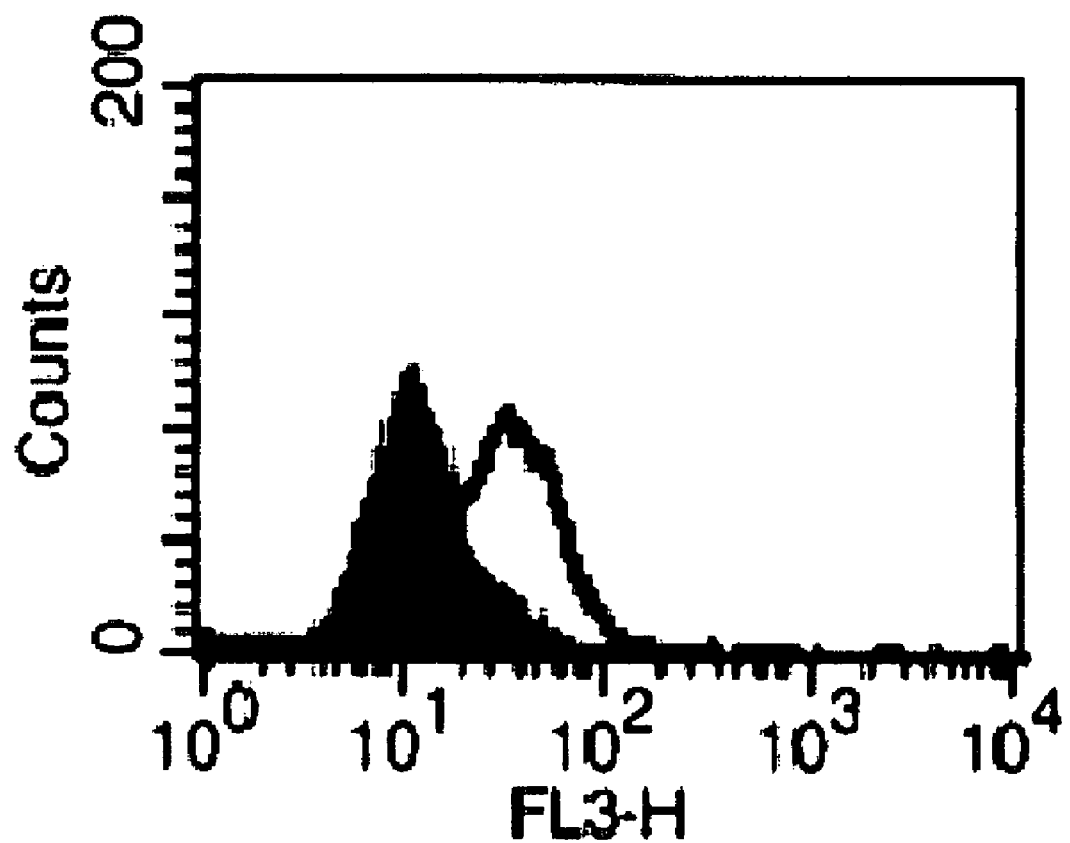
FIG. 2 is a scatter-plot graph depicting mean fluorescence intensity following FACS analysis of cells transfected with either unlabeled (black fill) or Cy3-labeled (no fill) siRNA.

Fluorescent cytoplasmic granules were observed in VSMCs transfected with Cy3-siRNA (FIG. 1B), indicating successful transfection was accomplished. Nearly all cells transfected with Cy3-labeled siRNA demonstrated clear cytoplasmic granules, whereas cells transfected with unlabeled siRNA demonstrated only faint background autofluorescence (FIG. 1A). These findings were confirmed by an independent blinded investigator. Transfection efficiency of human VSMC was 91±5% as determined by FACS analysis. The mean fluorescence intensity for unlabeled cells was 14.3±0.5 compared to 37.2±4.5 ($p<0.0001$). Each curve was unimodal suggesting a homogenous population of cells (FIG. 2).

Example 2

Inhibiting MARCKS Activity with a PKC-Inhibitor Decreases Cellular Migration and Proliferation of VSMCs in Culture Materials and Methods To assess cellular migration, a fluorescent migration assay (BD Biosciences, San Jose, Calif.) was utilized. In this assay, VSMC's grown in culture were labeled with 1 µM calcein. Approximately 50,000 cells, suspended in serum free media, were loaded onto a 0.3 $cm^2$ insert. The surface of the insert is a fluorescently-opaque polyethylene terephthalate (PET) membrane with 8 µm pores that are sufficiently large to permit cells to migrate across its surface. The insert was placed in a tissue culture plate with a chemotactic stimulus, TNF-α, in the lower well, which contained media with 30% FBS and TNF-A at a concentration of 200 Units/ml. Immediately after the inserts were placed into the respective wells, the wells were excited at a wavelength of 485 nm and the fluorescence emission was read at 535 nm. At the order of magnitude of cells that were used, the fluorescence is proportional to cell number in a linear relationship. After 24 hours, the plate was excited a second time and emission at 535 nm was read. Fluorescence was read only from the bottom well, such that only cells that have migrated contribute to the measured fluorescence. The proportion of cells that migrated was determined by dividing the fluorescence of the bottom of the wells at 24 hours by the initial fluorescence from the top of the wells at the time of plating. To account for passive diffusion across the membrane, inserts with no chemotactic stimulus in the lower well were analyzed, which served as a negative control.

Cellular proliferation was assessed using an alamarBlue Assay. alamarBlue is a compound which gains electrons from the highly reduced environment of actively proliferating cells. When it is reduced, it emits fluorescence at 590 nm. Therefore, emission at 590 nm was used as a marker for relative cellular proliferation. Cells were incubated in the dark in media containing 10% alamarBlue (BioSource International, Carmilla, Calif.) and 10% FBS for four hours. After incubation, 1 ml of media from the incubated cells was mixed with 1 ml of media containing 10% FBS and the emission at 590 nm was recorded.

A time-zero alamarBlue Assay was performed after a 12-hour period of starvation to assure equal cell loading and synchronization in the cell cycle. The cells were incubated with predetermined concentrations of the PKC inhibitor, 20-28. Cells were incubated in media with 30% FBS for a total of 24 hours. At that point, alamarBlue assays were performed at predetermined intervals. After each assay was completed, the media was replenished with media containing 30% FBS. As in the migration assay, an unstimulated, negative control with standard media was assayed.

To inhibit the effects of MARCKS activity, cells in culture were treated with the protein kinase C inhibitor 20-28 (Calbiochem, La Jolla, Calif.). The molecule 20-28 is a peptide pseudosubstrate of PKC which has been shown to inhibit phosphorylation of MARCKS in vivo. Eichholtz, T. et al. (1993) *J. Biol. Chem.* 268:1982-1986.

Results

Figure 3:
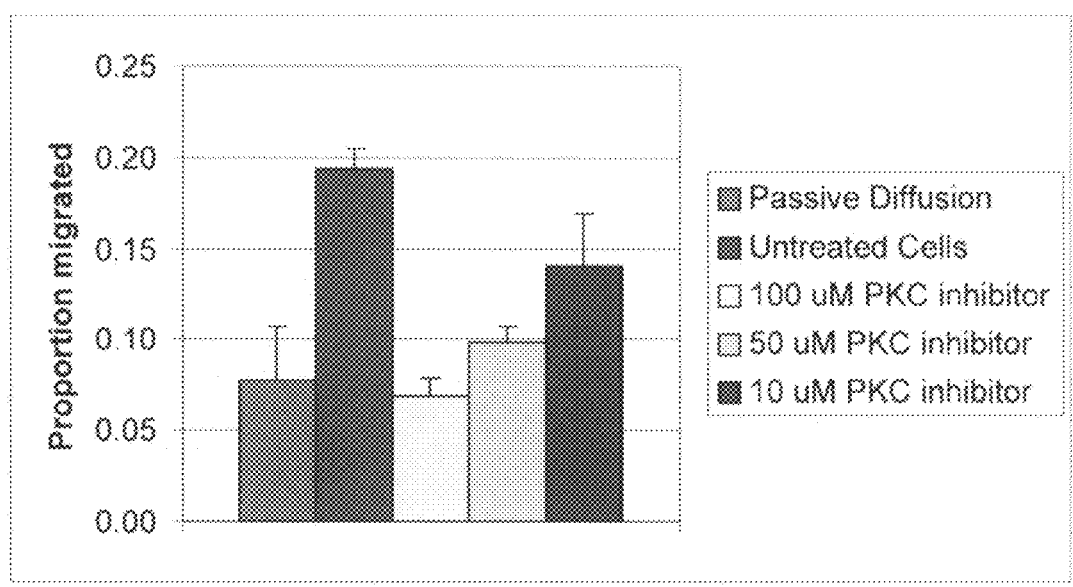
FIG. 3 is a bar graph demonstrating that treatment of VSMCs in culture with the protein kinase C pseudosubstrate, 20-28, inhibited VSMC migration in a fluorescent assay. The inhibitory effects of 20-28 were dose-dependent.

Incubation of VSMCs with the protein kinase C inhibitor 20-28 for 24 hours, at concentrations ranging from 10 µM to 100 µM, decreased both FBS and TNF-α stimulated migration. In untreated cells, 19.4%±5.1% migrated across the membrane, while treatment with 100 µM of the protein kinase C inhibitor reduced the migration across the membrane to 6.9%±1.5% ($p<0.001$). The proportion of cells migrating across the membrane after treatment with this concentration of protein kinase C inhibitor was the same as untreated cells in the absence of a chemotactic stimulus, 7.8%±2.1% (p=NS). These data are presented in FIG. 3.

Figure 4:
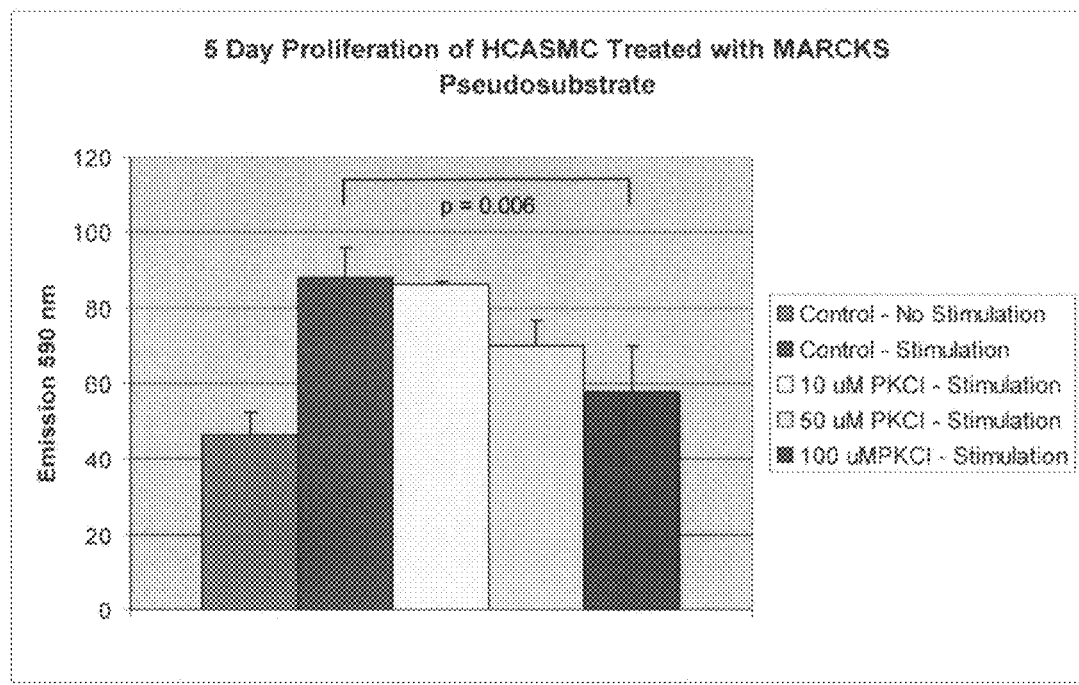
FIG. 4 is a bar graph demonstrating that treatment of VSMCs in culture with the protein kinase C pseudosubstrate, 20-28, inhibited VSMC proliferation. The inhibitory effects of 20-28 were dose-dependent.

VSMC proliferation was assessed in the presence of the protein kinase C inhibitor, 20-28. This antagonist significantly decreased serum-induced VSMC proliferation (FIG. 4). After 5 days of serum stimulation, untreated cells demonstrated an emission at 590 nm of 88.0±7.9 and cells receiving 100 µM of inhibitor demonstrated an emission at 590 nm of 58.0±12.1 (p=0.006). These maximally treated cells had an emission that was not statistically different from the untreated, unstimulated cells, e.g., 46.4±6.0 (p=NS). The inhibition of proliferation was dose-dependent. These data are presented in FIG. 4.

Example 3

Testing the Effects of RNA Inhibition of a MARCKS-Family Gene on the Migration and Proliferation of VSMCs in Culture Transfection of vascular smooth muscle cells in culture with siRNA having homology to an RNA transcript of a MARCKS-family gene is performed as described in Example 1. The effects of the siRNA on VSMC migration and proliferation in transfected cells is assessed using the migration and proliferation assays described in Example 2. A decrease in cellular migration or proliferation in cells transfected with MARCKS siRNA, relative to control cells that have been transfected with control siRNA, would indicate that inhibiting expression of the MARCKS-family gene can inhibit these cellular processes.

To ensure that expression of the MARCKS-family gene is inhibited by the siRNA, Western blot analysis is performed to determine whether cellular levels of the MARCKS-family protein are reduced in transfected cells. An example of a suitable protocol for such an assay is described herein. Protein is extracted from VSMCs growing in culture. Cells are harvested from culture dishes with a 9.6 cm$^2$ growth area, lifted from a plate with 500 µl trypsin and quenched with an equal volume of media containing 10% fetal bovine serum (FBS). After trypsinization the cell suspension is centrifuged to form a cellular pellet which subsequently is lysed in 75 µl RIPA lysis buffer containing a proteinase inhibitor cocktail. After a 30 minute incubation on ice, the lysed cells are centrifuged, leaving soluble protein in the supernatant. The supernatant is collected and total protein concentration in each sample is assessed using a standard Lowry Assay.

The protein samples is mixed with loading buffer in a 1:4 ratio and 20 to 40 µg of protein from each sample is loaded into their respective wells on a polyacrylamide gel. The protein electrophoresis is run at 70 volts for a period of 60 to 90 minutes, allowing adequate separation of protein. The protein is then transferred to a nitrocellulose membrane by applying a current of 0.04 amps to the gel and membrane for 60 minutes. After the transfer, the nitrocellulose membrane is blocked using a 5% milk solution in PBS/0.1% TWEEN 20 for 60 minutes. The antibody directed against the protein of interest (e.g., the MARCKS-family member protein) is incubated with the membrane at a concentration of 1 µg antibody in 3000 µl milk solution. After 12 hours of incubation at 4° C., the membrane is washed with PBS/TWEEN 20 for 30 minutes. Next, a secondary antibody conjugated with horseradish peroxidase is incubated with the membrane for 60 minutes. Once again the membrane is washed for 30 minutes. The membrane is treated with chemiluminescent reagents and the Western Blot is developed using Kodak XO Mat film processor.

Example 4

Figure 5A:
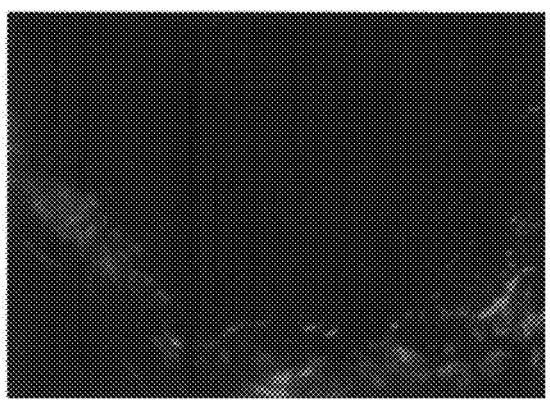
FIG. 5A is a fluorescent image of a section of human saphenous vein transfected with unlabeled siRNA. Cells are shown at 40× magnification.
Figure 5B:
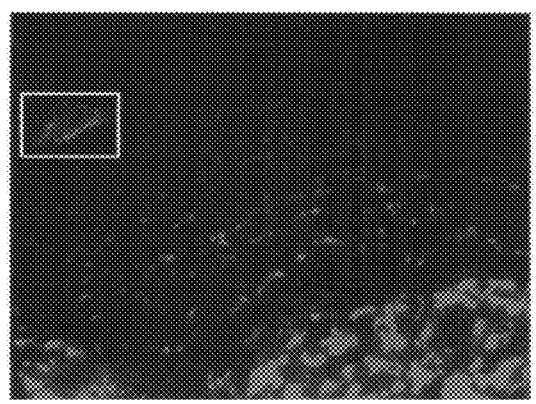
FIG. 5B is a fluorescent image of a section of human saphenous vein transfected with Cy3-labeled siRNA. Cells are shown at 40× magnification. Fluorescent granules of siRNA are visible in the media of the transfected vein.

Transfection of Vascular Smooth Muscle Cells (VSMCs) from a Vein Graft with siRNA Decreases VSMC Proliferation Materials and Methods Transfection of human saphenous vein with Cy3-labeled siRNA was accomplished using freshly harvested human saphenous vein discarded from the operating room. Vein segments were transfected with a nondistending pressure of 0.4 ATM for one hour at room temperature. These segments were mounted in OCT, frozen in liquid nitrogen, and sectioned on a cryotome. The sections were mounted on poly-L-lysine slides and prepared with mounting medium (Vectashield, Vector, Burlingame, Calif.). The slides were visualized with a fluorescent microscope with an excitation wavelength of 550 nm and an emission wavelength of 570 nm. In sections treated with Cy3-labeled siRNA, fluorescent granules could be observed studding the media of the vessel (see FIGS. 5A and 5B). The intima could not be assessed reliably using this methodology.

Results

Figure 6:
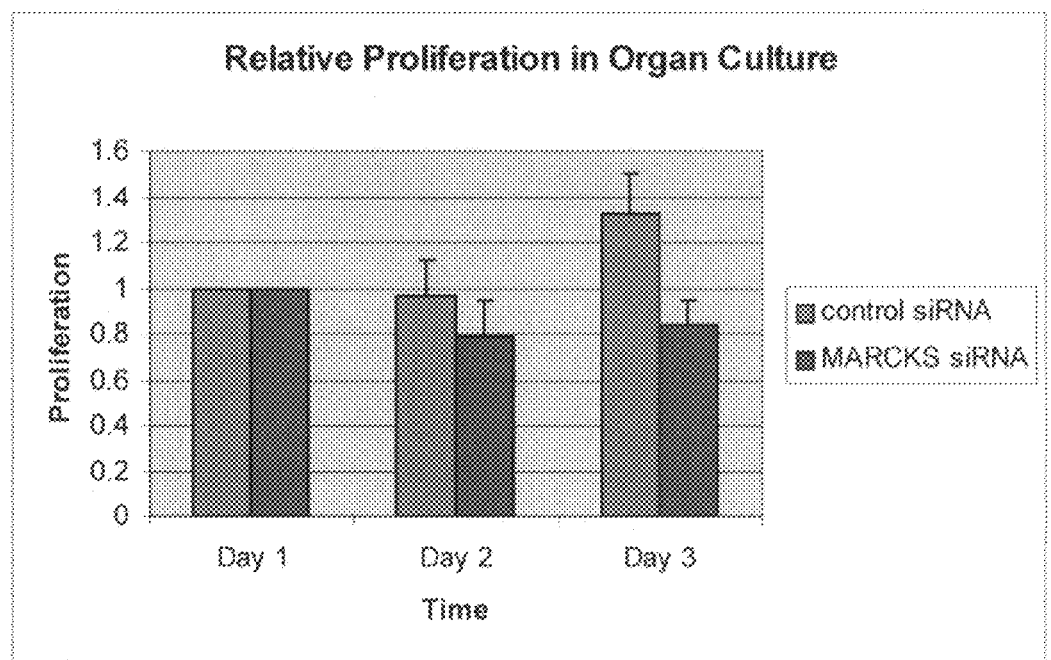
FIG. 6 is a bar graph depicting cellular proliferation in human saphenous vein transfected with 100 nM of either control or MARCKS siRNA. Three days after transfection, cells transfected with MARCKS siRNA displayed reduced proliferation relative to cells transfected with control RNA.

VSMCs in veins that were transfected with 100 nM Mac-MARCKS siRNA demonstrated statistically significant, arrested proliferation compared to cells treated with scrambled siRNA with sequence having no homology in the human genome (FIG. 6). Ex vivo transfection of whole vein decreased proliferation by 36.6% (p<0.0002) at 3 days post transfection.

Example 5 siRNA-Mediated Silencing of Gene Targets in Human Vein

Materials and Methods siRNA Design siRNA targeting the housekeeping gene glyceraldehyde 3-phosphate dehydrogenase (GAPDH) was purchased from Ambion (Austin, Tex.). All other siRNAs were purchased from Dharmacon (Lafayette, Colo.). Additional siRNAs were designed to target the TNF-a receptor 1 (TNFRSF1A siGENOME duplex 2). Non-targeting control siRNA (sense 5'-CGC ACC AGA ACA AAC ACA C-3' (SEQ ID NO. 5; Willis, D J et al. (2004) *Journal of Surgical Research* 120:27-36) was custom synthesized with dTdT overhangs on the 3' ends of both strands. Cy5-siRNA was synthesized by adding a 5'-Cy5 modification to the sense strand of the non-targeting control siRNA.

Transfection of Human Vein with siRNA

To determine if siRNA could be generally employed for silencing gene expression in human vein, the techniques of Mann et al. (ref. 31) were utilized. Excess saphenous vein from vascular procedures was transfected for 10 minutes at 0.4 ATM non-distending pressure using a syringe pressure chamber device fitted with a metered angioplasty insufflator and filled with 1 µM GAPDH or control siRNA resuspended in normal saline. After transfection, the vein segments were rinsed and placed in organ culture in VSMC media with 30% FBS. After 5 days in culture, vein segments were snap frozen and sectioned for immunohistochemistry (IHC) staining of GAPDH.

To assess the effect of pressure on siRNA transfection, the pattern of siRNA delivery in the vein wall was visualized after transfection with non-distending pressure at 0.4 ATM and compared to the pattern of siRNA delivery after luminal distension with siRNA solution at 120 mm Hg of pressure, a system intended to be analogous to the hydrodynamic tail vein method in the mouse, but regulated not to exceed the pressure of the arterial circulation where the vein graft would eventually reside, or the pressure where injury to vein grafts has been demonstrated to occur (Davies, MG and Hagen, PO (1995) *Eur. J. Vasc. Endovasc. Surg.* 9(1):7-18). siRNA labeled with a fluorescent Cy5 tag or control siRNA was suspended in normal saline solution and delivered to human vein segments for 10 minutes using either the non-distending or distending pressure methods. Parallel segments were also soaked in siRNA solution for 10 minutes without any pressure treatment to serve as control. After transfection, vein segments were rinsed and placed in organ culture for 4 hours, then snap frozen and sectioned for confocal microscopy.

To determine if differences in bulk siRNA delivery led to differences in mRNA knockdown, vein segments were transfected for 10 minutes with either 1 µM control siRNA or 1 µM siRNA targeting the TNF-α receptor 1 (TNFaRSF1) by soaking (Soak) or by transfecting under non-distending (NDP) or distending pressure (DP). After transfection, vein segments were rinsed and placed in organ culture for 48 hours, at which point they were homogenized for RNA extraction and subsequent analysis of TNFaRSF1 mRNA levels by qRT-PCR.

Evaluation of mRNA Knockdown

Evaluation of target gene mRNA knockdown after siRNA delivery was analyzed using a Stratagene MX3000P real time PCR (qRT-PCR) machine (Stratagene, La Jolla, Calif.). Total RNA was extracted from plate wells or homogenized vein segments using RNeasy spin columns (Qiagen, Valencia, Calif.) and cDNA was prepared from 1 µl RNA using the iScript cDNA synthesis kit (Bio-Rad, Hercules, Calif.) prior to thermal cycling. For quantitative analysis, target gene levels were normalized to 18s levels as previously described, (Bustin, S A et al. (2004) *J. Mol. Endocrinol.* 29(1):23-39) and target and housekeeper gene amplification reactions were performed in triplicate for each cDNA sample using 1 µl cDNA per reaction. Target gene amplification was performed using Brilliant SYBR Green QPCR Reagent (Stratagene) and housekeeper gene amplification was performed in separate wells using Brilliant QPCR Master Mix (Stratagene) with gene-specific dual-labeled linear probes (IDT, Coralville, Iowa). Primer sequences, probe sequences, and final oligonucleotide concentrations used are as follows:

| Gene | Primer/Probe Sequences | Concentration (nM) |
|---|---|---|
| GAPDH | (f) 5'- AGT CAG CCG CAT CTT CTT TTG - 3' (SEQ ID NO. 6) | 300 |
|  | (r) 5'- CGC CCA ATA CGA CCA AAT CC - 3' (SEQ ID NO. 7) | 300 |
| TNFRS1A | (f) 5'- CCT TTT ATC CCT CCT CTT CAT TGG - 3' (SEQ ID NO. 8) | 300 |
|  | (r) 5'- GTG TCG ATT TCC CAC AAA CAA TG - 3' (SEQ ID NO. 9) | 300 |
| 18s | (f) 5'- GTT GAT TAA GTC CCT GCC CTT TG - 3' (SEQ ID NO. 10) | 30 |
|  | (r) 5'- TAG TCA AGT TCG ACC GTC TTC TC - 3' (SEQ ID NO. 11) | 30 |
|  | Probe: 5'- Hex/CAC ACC GCC CGT CGC TAC TAC CG/IABlkFQ - 3' (SEQ ID NO. 12) | 100 |
| $B_2M$ | (f) 5'- CTC CAC AGG TAG CTC TAG GAG - 3' (SEQ ID NO. 13) | 300 |
|  | (r) 5'- TCT GAC CAA GAT GTT GAT GTT GG - 3' (SEQ ID NO. 14) | 300 |

-continued

| Gene | Primer/Probe Sequences | Concentration (nM) |
|---|---|---|
|  | Probe:<br>5'- Hex/TCT CTG CTC CCC ACC TCT AAG TTG CCA/IAB1kFQ - 3'<br>(SEQ ID NO. 15) | 300 |

Thermal cycling was performed under the following conditions: Stage 1: 10 minutes at 95° C.; Stage 2 (40 cycles): 30 seconds at 95° C., 1 minute at 60° C., 30 seconds at 72° C. The Comparative Quantification software tool was used to compare normalized gene levels from cells transfected with targeting siRNA vs. non-targeting control siRNA (calibrators). Plate-specific standard curves were generated for both target and housekeeper gene amplification reactions and used to calibrate the Comparative Quantification software tool.

Histology and Immunohistochemistry

The vein grafts and control veins were processed in ethanol and embedded in paraffin. Six μm sections were cut and stained with hematoxylin-eosin. For immunohistochemistry, tissue sections were deparaffinized in xylene and rehydrated in graded alcohol. Heated citrate buffer antigen retrieval was performed when necessary. Sections were treated with 3% hydrogen peroxide. Non-serum protein blocking was followed by incubation overnight with primary antibody. Specimens were washed with PBS and the alkaline phosphatase conjugated secondary antibody applied for 30 minutes followed by the chromagen red substrate for 10 minutes. Slides were counterstained with hematoxylin and mounted with aqueous mounting media.

Statistical Methods

All experiments were performed in triplicate unless otherwise noted. Data are presented as means with standard deviation. Statistical analysis was performed using STATA software (STATA Corporation). Significance of association was assessed using the two-tailed Student t test (unpaired) or linear regression where appropriate.

Results

Figures 7A, 7B:
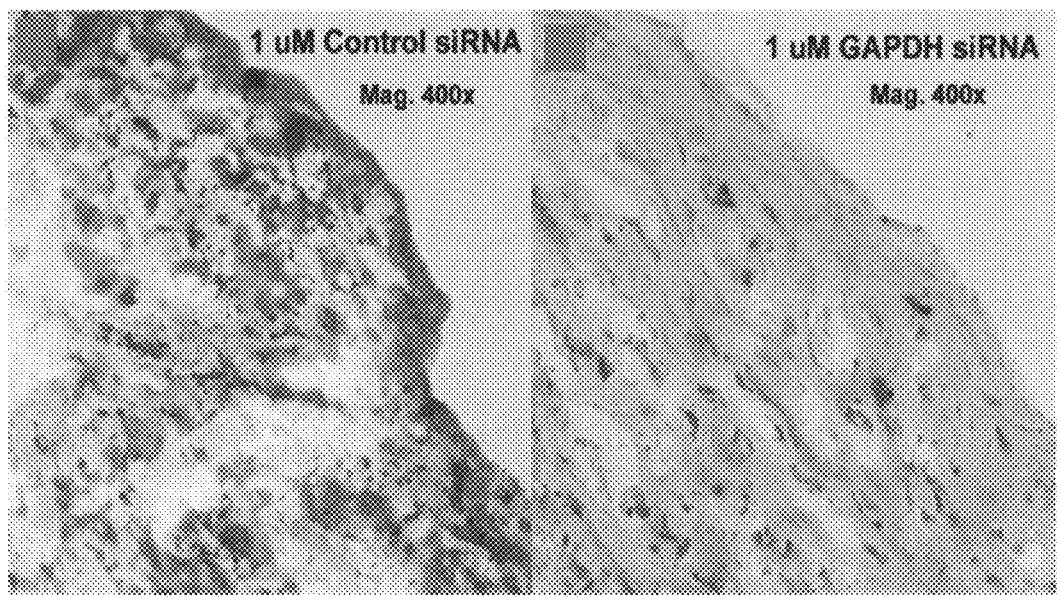
FIG. 7A is a representative micrograph at 400× magnification depicting immunohistochemical (IHC) staining of GAPDH in a cross section of human saphenous vein after treatment with 1 µM control non-targeting siRNA.
FIG. 7B is a representative micrograph at 400× magnification depicting IHC staining of GAPDH in a cross section of human saphenous vein after treatment with 1 µM GAPDH siRNA showing decreased levels of GAPDH protein relative to human vein that was treated with control non-targeting siRNA (see FIG. 7A).
Figure 8:
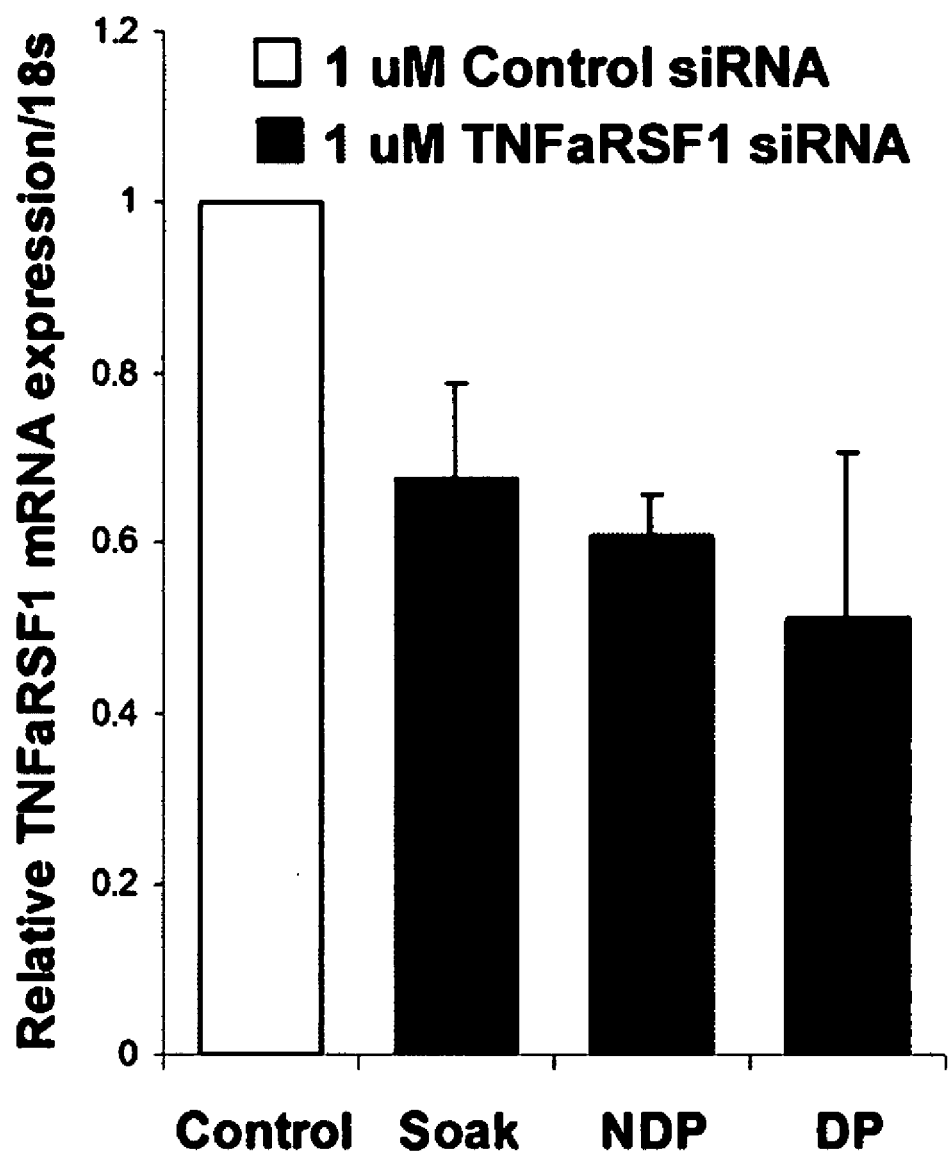
FIG. 8 is a bar graph depicting TNF-A receptor 1 (TNFaRSF1) mRNA knockdown in human vein segments following transfection for 10 minutes with either 1 µM control siRNA (Control) or 1 µM TNFaRSF1 siRNA by soaking the vein in siRNA solution (Soak) or by using either non-distending pressure (NDP) or distending pressure (DP). The graph shows siRNA-mediated knockdown of TNFaRSF1 mRNA using all 3 transfection methods (black bars) relative to the control (white bar).

Clear evidence of GAPDH protein silencing in human saphenous vein was seen upon IHC visualization after transfection of siRNA with non-distending pressure (FIGS. 7A, 7B). Moreover, significant knockdown of TNFaRSF1 mRNA was observed after all three transfection treatments, ranging from 32±11% knockdown with the soak treatment to 49±20% knockdown after distending pressure transfection (FIG. 8).

Figures 9A, 9B:
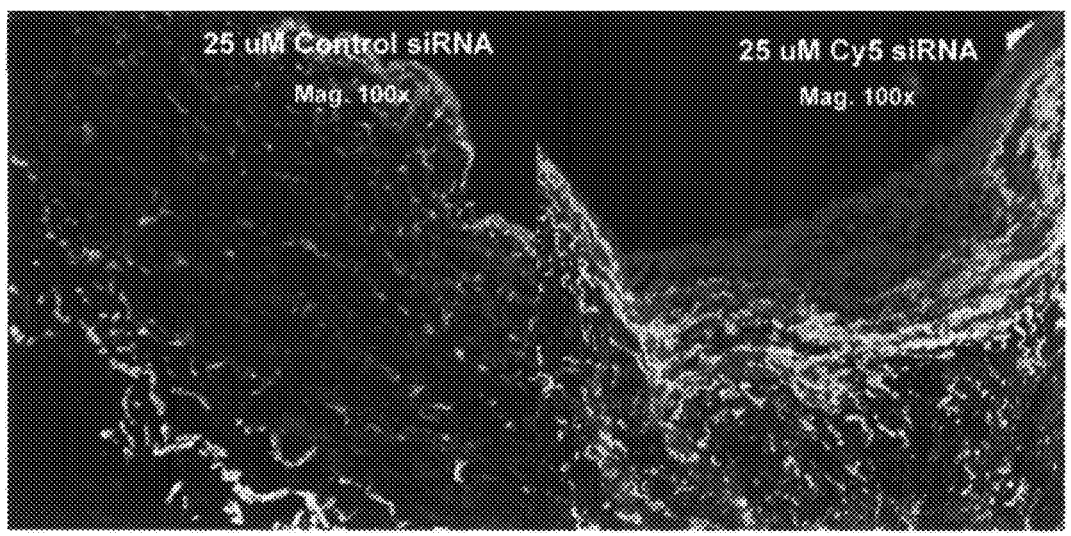
FIG. 9A is a representative confocal micrograph at 100× magnification of a human vein segment after transfection with 25 µM control siRNA. The observed fluorescence is due to autofluorescence of elastic fibers.
FIG. 9B is a representative confocal micrograph at 100× magnification of a human vein segment after transfection with 25 µM Cy5-labeled siRNA. Enhanced fluorescence relative to the image in FIG. 9A is due to uptake of the Cy5-labeled siRNA.
Figure 10:
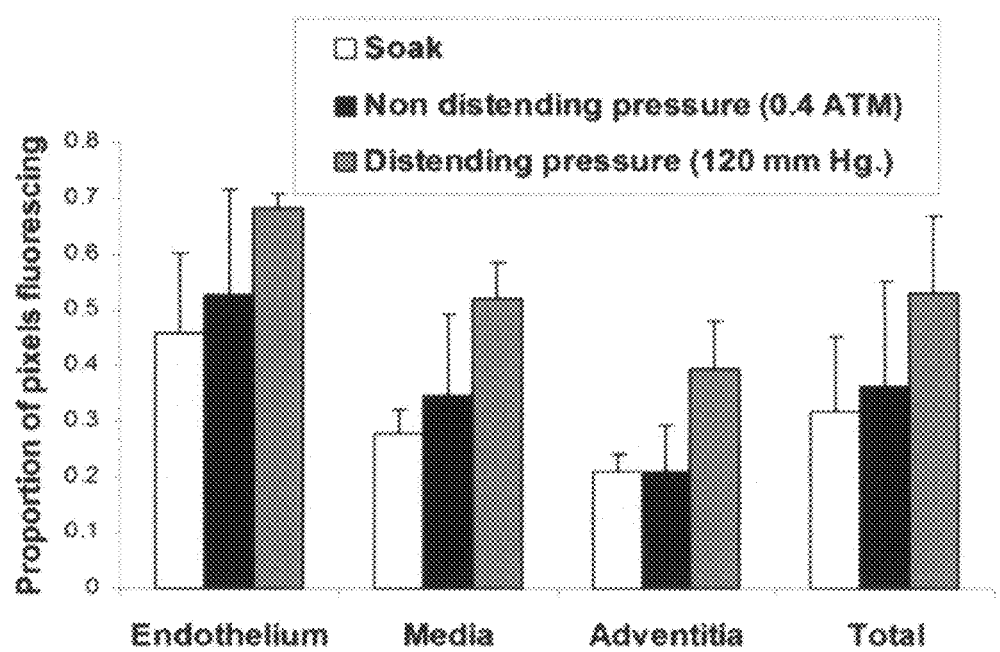
FIG. 10 is a bar graph depicting quantitation of Cy5 fluorescence in confocal micrographs according to cell layer, indicating significantly greater uptake of Cy5-labeled siRNA by the endothelium relative to the media or adventitia following transfection of vein segments by soaking the vein in siRNA solution (white bars) or by using either non-distending pressure (black bars) or distending pressure (grey bars). The total quantity of siRNA delivered to the cell wall was greatest using distending pressure, while no significant difference in siRNA uptake was observed between soaking and non-distending pressure transfection conditions.

Upon transfection of vein with Cy5-siRNA, all three transfection methods resulted in Cy5 fluorescence in a unique cellular pattern throughout the full thickness of the vein wall, which was discrete from the auto-fluorescence patterns of the elastic fibers, suggesting successful incorporation of siRNA into all vessel layers (FIGS. 9A, 9B). Quantitation of Cy5 fluorescence in confocal micrographs by cell layer demonstrated significantly greater uptake of siRNA by the endothelial layer compared to the media or adventitia (56±8% pixels fluorescing for endothelium compared to 38±6% and 27±3% for the media and adventitia respectively, P<0.0001 for all differences; FIG. 10), consistent with in vitro observations of superior gene silencing in HECs compared to HVSMCs (see Examples 7 and 8). In addition, the total quantity of siRNA delivered to the vein wall was greatest using distending pressure transfection (53±14% pixels fluorescing). There was no significant difference in the quantity of siRNA delivered between segments transfected with non-distending pressure and those simply soaked in siRNA solution (36±19% vs. 32±14%; P=NS; FIG. 10).

These data demonstrate that vein grafts are competent for rapid siRNA transfection and gene silencing under conditions amenable to current operative technique. These data further suggest that siRNA transfection using distending pressure might be more effective for achieving high levels of gene knockdown than simply soaking the vein graft in a siRNA solution, which might be sufficient for achieving low levels of gene silencing.

Example 6

Expression of MARCKS is Up-Regulated in Clinical Samples of Human Vein Graft Disease Materials and Methods Samples To help elucidate whether graft remodeling results in pathologic changes in MARCKS gene expression, MARCKS expression levels were measured in clinical samples of human vein graft disease. With Institutional Review Board (IRB) approval, 7 pairs of samples of failed human vein grafts were collected, with paired control vein, from patients undergoing either lower extremity graft revision or lower extremity amputation after graft failure. Once collected, the samples were processed for RNA and protein extraction to yield material suitable for various downstream measures of gene and protein expression.

Evaluation of MARCKS mRNA Expression

Evaluation of target gene mRNA expression was analyzed using a Stratagene MX3000P real time PCR (qRT-PCR) machine (Stratagene, La Jolla, Calif.). Total RNA was extracted from plate wells using RNeasy spin columns (Qiagen, Valencia, Calif.) and cDNA was prepared from 1 μl RNA using the iScript cDNA synthesis kit (Bio-Rad, Hercules, Calif.) prior to thermal cycling. For quantitative analysis, target gene levels were normalized to 18s or $B_2M$ levels as previously described (Bustin, S A et al. (2004) *J. Mol. Endocrinol.* 29(1):23-39) and target and housekeeper gene amplification reactions were performed in triplicate for each cDNA sample using 1 μl cDNA per reaction. Target gene amplification was performed using Brilliant SYBR Green QPCR Reagent (Stratagene) and housekeeper gene amplification was performed in separate wells using Brilliant QPCR Master Mix (Stratagene) with gene-specific dual-labeled linear probes (IDT, Coralville, Iowa). The primer sequences used for analysis of MARCKS expression were as follows: forward, 5'-CGG CAG AGT AAA AGA GCA AGC-3' (SEQ ID NO. 16); reverse, 5'-GGT TGT AGA CAA GTT CTC CAA AAC-3' (SEQ ID NO. 17). Each primer was used at a 300 nM concentration.

Thermal cycling was performed under the following conditions: Stage 1: 10 minutes at 95° C.; Stage 2 (40 cycles): 30 seconds at 95° C., 1 minute at 60° C., 30 seconds at 72° C. The Comparative Quantification software tool was used to compare normalized gene levels from cells transfected with targeting siRNA vs. non-targeting control siRNA (calibrators). Plate-specific standard curves were generated for both target and housekeeper gene amplification reactions and used to calibrate the Comparative Quantification software tool.

Statistical Methods

All experiments were performed in triplicate unless otherwise noted. Data are presented as means with standard deviation. Statistical analysis was performed using STATA software (STATA Corporation). Significance of association was assessed using the two-tailed Student t test (unpaired) or linear regression where appropriate.

Results

Figure 11:
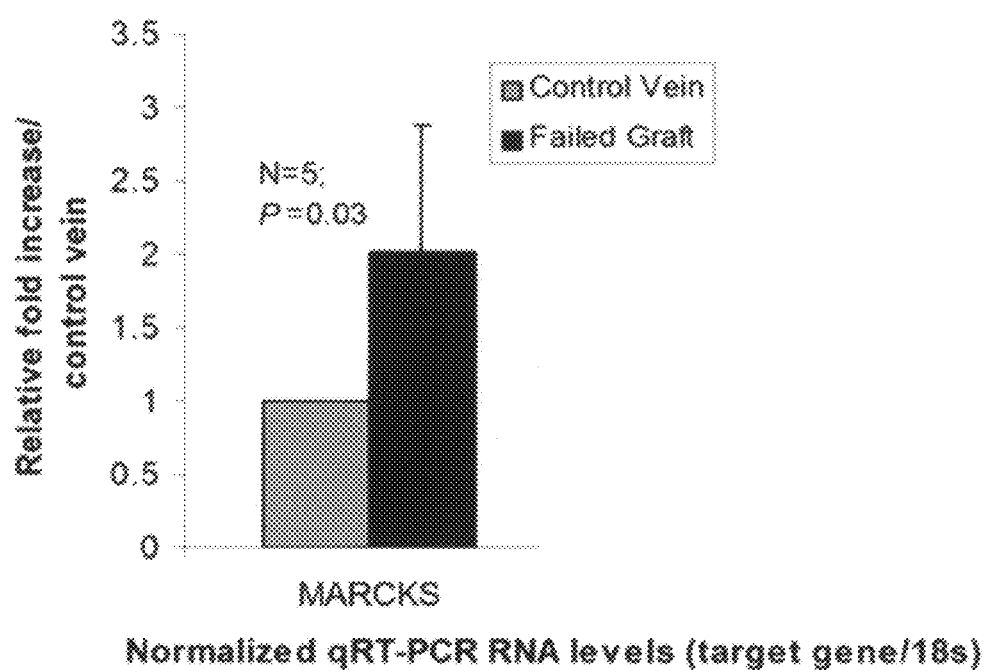
FIG. 11 is a bar graph depicting increased expression of MARCKS mRNA in failed human vein graft tissues (black bar) from 5 patients relative to patient-matched control veins (grey bar), as determined by qRT-PCR analysis. mRNA levels were normalized to 18s RNA levels.

Levels of MARCKS mRNA expression were up-regulated in the majority of the failed human vein graft samples, relative to MARCKS mRNA expression levels in control vein from the same patient (FIG. 11). In particular, qRT-PCR analysis identified a 2-fold increase (2.0±0.9; P=0.03) in MARCKS mRNA levels in failed human vein grafts when compared to matched control vein in 5 out of 7 sets of patient samples (FIG. 11).

Example 7 siRNA-Mediated Gene Knockdown of MARCKS Results in Decreased Proliferation and Migration of Vascular Cells In Vitro Materials and Methods Cell Culture Human vascular smooth muscle cells (HVSMCs) and endothelial cells (HECs) were purchased from Cambrex (Walkersville, Md.) and cultured in smooth muscle cell (SmGM-2 BulletKit; Cambrex) or endothelial cell (EGM-2 BulletKit; Cambrex) media as per manufacturer's recommendations. All experiments were performed between passages 5 and 8 for both cell types.

siRNA Design siRNA targeting the housekeeping gene glyceraldehyde 3-phosphate dehydrogenase (GAPDH) was purchased from Ambion (Austin, Tex.). All other siRNAs were purchased from Dharmacon (Lafayette, Colo.). Additional siRNAs were designed to target the TNF-α receptor 1 (TNFRSF1A siGENOME duplex 2) and the myristoylated alanine-rich C kinase substrate (MARCKS siGENOME duplex 4). A single siRNA sequence that targets the MARCKS transcript has been used, (5'-GGU-GCC-CAG-UUC-UCC-AAG-AUU-3' [sense] (SEQ ID NO. 18), 5'-UCU-UGG-AGA-ACU-GGG-CAC-CUU-3' [anti-sense] (SEQ ID NO. 19). The anti-sense strand is additionally modified with a phosphate group at the 5' end. Non-targeting control siRNA (sense 5'-CGC ACC AGA ACA AAC ACA C-3' (SEQ ID NO. 5); Willis, D J et al. (2004) *Journal of Surgical Research* 120:27-36) was custom synthesized with dTdT overhangs on the 3' ends of both strands. Cy5-siRNA was synthesized by adding a 5'-Cy5 modification to the sense strand of the non-targeting control siRNA.

siRNA Lipofection

MARCKS knockdown was achieved by lipofection of HVSMCs and HECs with MARCKS siRNA. Lipofection was performed using the DharmAFECT1 transfection reagent (Dharmacon) for 24 hours in serum- and antibiotic-free media as per manufacturer's protocol.

Evaluation of mRNA Knockdown

Evaluation of target gene mRNA knockdown after siRNA delivery was analyzed using a Stratagene MX3000P real time PCR (qRT-PCR) machine (Stratagene, La Jolla, Calif.). Total RNA was extracted from plate wells using RNeasy spin columns (Qiagen, Valencia, Calif.) and cDNA was prepared from 1 μl RNA using the iScript cDNA synthesis kit (Bio-Rad, Hercules, Calif.) prior to thermal cycling. For quantitative analysis, target gene levels were normalized to 18s or $B_2M$ levels as previously described (Bustin, S A et al. (2004) *J. Mol. Endocrinol.* 29(1):23-39), and target and housekeeper gene amplification reactions were performed in triplicate for each cDNA sample using 1 μl cDNA per reaction. Target gene amplification was performed using Brilliant SYBR Green QPCR Reagent (Stratagene) and housekeeper gene amplification was performed in separate wells using Brilliant QPCR Master Mix (Stratagene) with gene-specific dual-labeled linear probes (IDT, Coralville, Iowa). Primer sequences, probe sequences, and final oligonucleotide concentrations used are as follows:

| Gene | Primer/Probe Sequences | Concentration (nM) |
|---|---|---|
| GAPDH | (f) 5'- AGT CAG CCG CAT CTT CTT TTG - 3' (SEQ ID NO. 6) | 300 |
| | (r) 5'- CGC CCA ATA CGA CCA AAT CC - 3' (SEQ ID NO. 7) | 300 |
| MARCKS | (f) 5'- CGG CAG AGT AAA AGA GCA AGC - 3' (SEQ ID NO. 16) | 300 |
| | (r) 5'- GGT TGT AGA CAA GTT CTC CAA AAC - 3' (SEQ ID NO. 17) | 300 |
| 18s | (f) 5'- GTT GAT TAA GTC CCT GCC CTT TG - 3' (SEQ ID NO. 10) | 30 |
| | (r) 5'- TAG TCA AGT TCG ACC GTC TTC TC - 3' (SEQ ID NO. 11) | 30 |
| | Probe: 5'- Hex/CAC ACC GCC CGT CGC TAC TAC CG/IAB1kFQ - 3' (SEQ ID NO. 12) | 100 |

-continued

| Gene | Primer/Probe Sequences | Concentration (nM) |
|---|---|---|
| $B_2M$ | (f) 5'- CTC CAC AGG TAG CTC TAG GAG - 3' (SEQ ID NO. 13) | 300 |
| | (r) 5'- TCT GAC CAA GAT GTT GAT GTT GG - 3' (SEQ ID NO. 14) | 300 |
| | Probe: 5'- Hex/TCT CTG CTC CCC ACC TCT AAG TTG CCA/IAB1kFQ - 3' (SEQ ID NO. 15) | 300 |

Thermal cycling was performed under the following conditions: Stage 1: 10 minutes at 95° C.; Stage 2 (40 cycles): 30 seconds at 95° C., 1 minute at 60° C., 30 seconds at 72° C. The Comparative Quantification software tool was used to compare normalized gene levels from cells transfected with targeting siRNA vs. non-targeting control siRNA (calibrators). Plate-specific standard curves were generated for both target and housekeeper gene amplification reactions and used to calibrate the Comparative Quantification software tool.

Cell Migration and Proliferation Assays

The migratory and proliferative abilities of HVSMCs and HECs were assessed after MARCKS knockdown using migration and proliferation assays. Phenotypic analysis of HVSMC migration was performed using the Fluoroblok migration assay (BD Biosciences, San Jose, Calif.) to measure the ability of calcein-AM fluorescently-labeled cells to migrate through a PET membrane with 8 µM pores towards a chemotactant stimulus of 30% FBS. Briefly, VSMCs were incubated in 10 µM calcein-AM (Invitrogen) for 1 hour, trypsinized, and resuspended in serum-free VSMC media. In this assay, the upper chamber of the Transwell insert is separated from the lower chamber by a fluorescently opaque polyethyleneterephthalate (PET) membrane with 8 µm pores at the base of the insert. Approximately 50,000 VSMCs were loaded in each of the upper wells. The lower wells contained media supplemented with serum-free VSMC media, VSMC media with 30% FBS, or EC-conditioned media to stimulate cell migration. At time 0, the upper chambers were read at an excitation of 485 nm and an emission of 535 nm on a Biotek Fluorometer FLX800 (BioTek Instruments) and returned to the incubator. After 24 hours, the lower chambers were read with the same settings. The proportion of cells migrated were calculated by dividing the fluorescent intensity after 24 hours by the intensity read at time 0.

For HECs, the migration assay was modified to use a PET membrane with 3 µM pores and a chemoattractant stimulus of 5% FBS with 200 ng/ml VEGF. Migration assays for both cell types were performed 3 days after lipofection with MARCKS siRNA at concentrations shown to achieve complete MARCKS protein knockdown.

Phenotypic analysis of vascular cell proliferation was performed using the alamarBlue assay (Trek Diagnostics, Cleveland, Ohio), as previously described (Voytik-Harbin, SL et al. (1998) In Vitro Cell Dev. Biol. Anim. 34(3):239-246), to quantitate total cellular metabolic activity in the wells of tissue culture plates. Briefly, HVSMCs were plated on 24-well plates at a density of 10,000 cells per well and grown for 24 hours in normal cell media. Afterwards, a Day 0 measurement of fluorescent intensity after 4 hour incubation with the alamarBlue reagent was obtained prior to siRNA lipofection. 24 hour siRNA lipofection in serum-free media served as the starvation period to synchronize cells in the cell cycle, followed by the application of media with 30% FBS to stimulate proliferation. AlamarBlue assays were performed every two days, followed by the reapplication of fresh media with 30% FBS. For analysis, the fluorescence intensity of each well was determined using an LS-5B Luminescence Spectrometer (PerkinElmer) at excitation and emission wavelengths of 509 and 590 nm, respectively, and was divided by the value obtained at Day 0 to generate a measure of relative proliferation.

Western Blots

To investigate the differential effects of MARCKS knockdown on the proliferation of vascular cells, Western blots were performed to assess $p27^{kip1}$ expression after the induction of proliferation in HVSMCs and HECs. To assess $p27^{kip1}$ expression in the setting of MARCKS knockdown, HVSMC and HECs were transfected with 25 nM Control (C) or MARCKS (M) siRNA followed by 48 hour starvation in media with 0.1% FBS to synchronize cells in the Go phase of the cell cycle. Proliferation was then induced by the addition of media with 30% FBS and cells were lysed 24 hours post-induction for protein harvest and Western blot analysis.

Cell extracts were recovered from 6-well plates after siRNA lipofection and analyzed by sodium dodecyl sulfate-polyacrylamide gel electrophoresis (SDS-PAGE) and Western blotting with the use of standard techniques. Antibodies used for protein detection were: mouse monoclonal anti-GAPDH (1:10,000 dilution, Ambion), goat polyclonal anti-MARCKS (N-19) IgG (1:100 dilution, Santa Cruz Biotechnology, Santa Cruz, Calif.), mouse monoclonal anti-$p27^{kip-1}$ (1:250 dilution, Pharmingen, San Diego, Calif.) and mouse anti-β-tubulin IgM (clone 5H1) (1:250 dilution, Pharmingen, San Diego, Calif.). Secondary antibodies used were peroxidase-conjugated goat anti-mouse IgG (H+L) (1:1,000-1:5,000 dilution, Chemicon International, Temecula, Calif.) and peroxidase-conjugated rabbit anti-goat IgG (H+L) (1:500 dilution, Bio-Rad). Densitometry was performed using Adobe Photoshop 6.0 or NIH Image J 1.34.

Statistical Methods

All experiments were performed in triplicate unless otherwise noted. Data are presented as means with standard deviation. Statistical analysis was performed using STATA software (STATA Corporation). Significance of association was assessed using the two-tailed Student t test (unpaired) or linear regression where appropriate.

Results

In light of the observed up-regulation of MARCKS expression in human vein grafts (see Example 6) and the known involvement of PKC signaling in vascular disease, the potential of MARCKS as a gene target for therapy was determined by assessing the effect of siRNA-mediated MARCKS knockdown on human vascular smooth muscle cell (HVSMC) and human vascular endothelial cell (HEC) phenotypes in vitro. In VSMCs, migration and proliferation are the two cardinal hallmarks of the transformed VSMC phenotype. While these two cellular processes do not address the inflammatory role of the endothelium in the pathogenesis of IH, HEC migration and proliferation were used as global indicators of overall HEC health and survival, critical factors that protect against the vessel injury response.

Figure 12A:
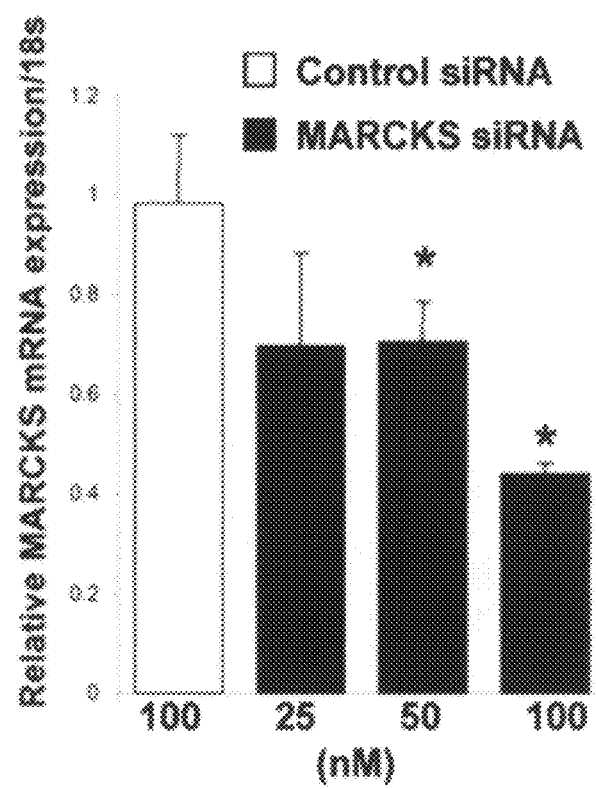
FIG. 12A is a bar graph depicting MARCKS mRNA knockdown, as determined by qRT-PCR, in human vascular smooth muscle cells 24 hours after lipofection of MARCKS siRNA at either 25, 50 or 100 nM concentrations (black bars) relative to transfection with 100 nM control scrambled siRNA (white bar). * denotes statistical significance.
Figure 12B:
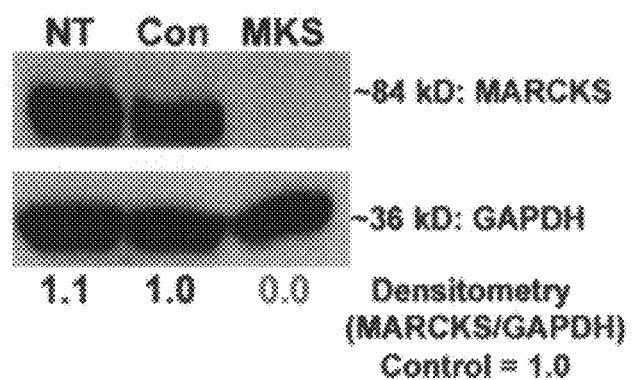
FIG. 12B is a Western blot depicting MARCKS protein levels in HVSMCs after no treatment (NT) or 3 days after lipofection with either 100 nM control siRNA (Con) or 100 nM MARCKS siRNA (MKS). Transfection with MARCKS siRNA resulted in complete knockdown of MARCKS expression. GAPDH protein levels were monitored as a loading control and used for corrected densitometry.
Figure 13A:
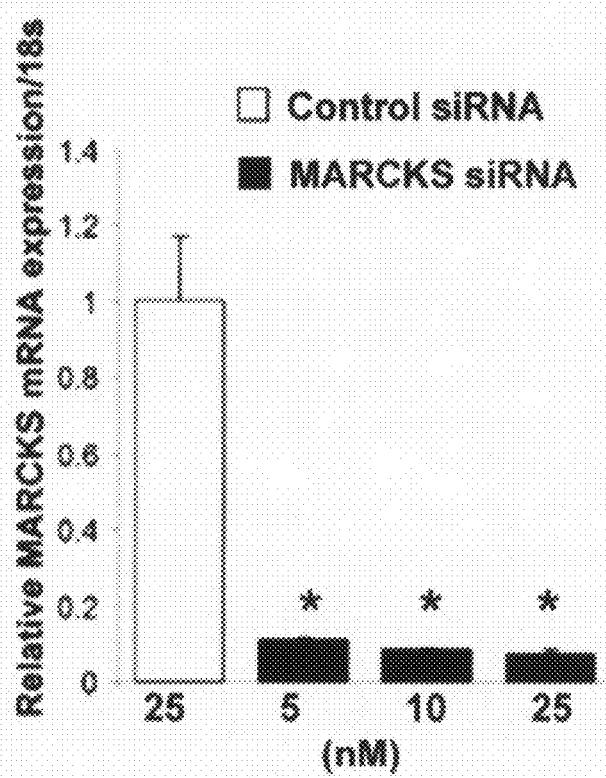
FIG. 13A is a bar graph depicting MARCKS mRNA knockdown, as determined by qRT-PCR, in human vascular endothelial cells (HEC) 24 hours after lipofection of MARCKS siRNA at 5, 10 or 25 nM concentrations (black bars) relative to transfection with 25 nM control scrambled siRNA (white bar). HECs were more susceptible than HVSMCs to MARCKS gene silencing at lower concentrations of siRNA. * denotes statistical significance.
Figure 13B:
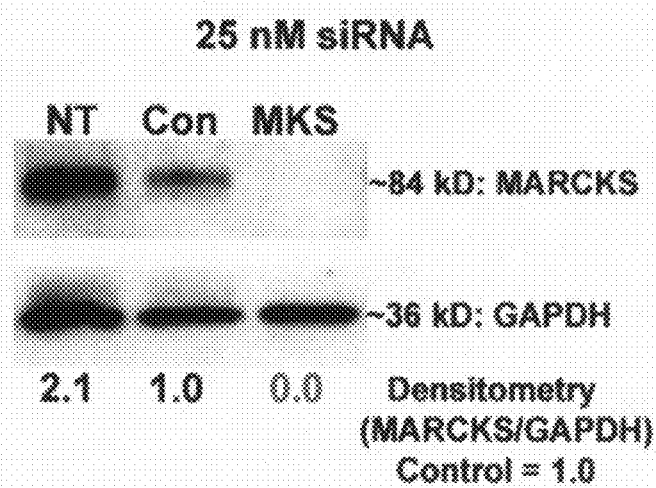
FIG. 13B is a Western blot depicting MARCKS protein levels in HECs after no treatment (NT) or 3 days after lipofection with either 25 nM control siRNA (Con) or 25 nM MARCKS siRNA (MKS). Transfection with MARCKS siRNA resulted in complete knockdown of MARCKS expression. GAPDH protein levels were monitored as a loading control and used for corrected densitometry.

The results of our studies demonstrated the effects of MARCKS knockdown in the two principal vascular cell types. In particular, HECs required only 5 nM MARCKS siRNA to achieve 89±1% (P=0.0008) knockdown 24 hours after lipofection (FIG. 13A), compared to HVSMCs where 24 hour mRNA knockdown levels only reached 54±2% (P=0.003) after lipofection with 100 nM siRNA (FIG. 12A). These data indicate that HECs have an increased susceptibility to siRNA gene silencing relative to HVSMCs. Analysis of MARCKS protein levels in both cell types after no treatment (NT), or lipofection with either control (Con) or MARCKS (MKS) siRNA demonstrated complete knockdown of MARCKS protein 3 days after lipofection with 100 nM MARCKS siRNA in HVSMCs (FIG. 12B) or 25 nM MARCKS siRNA in HECs (FIG. 13B).

Figure 14A:
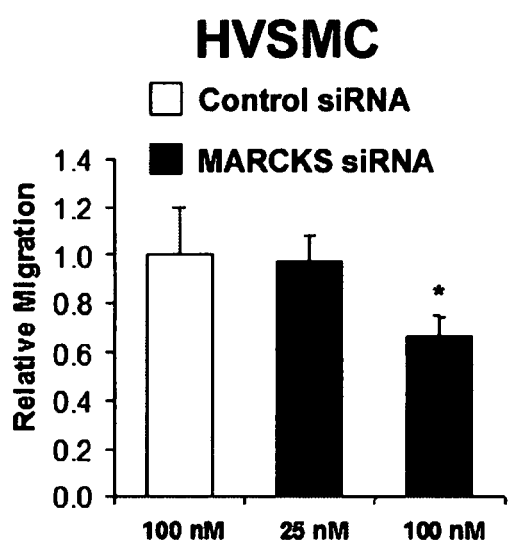
FIG. 14A is a bar graph depicting reduced cellular migration of HVSMCs upon silencing of MARCKS expression after transfection with 100 nM MARCKS siRNA, relative to cellular migration after transfection with either 100 nM control siRNA or 25 nM MARCKS siRNA. * denotes statistical significance.
Figure 14B:
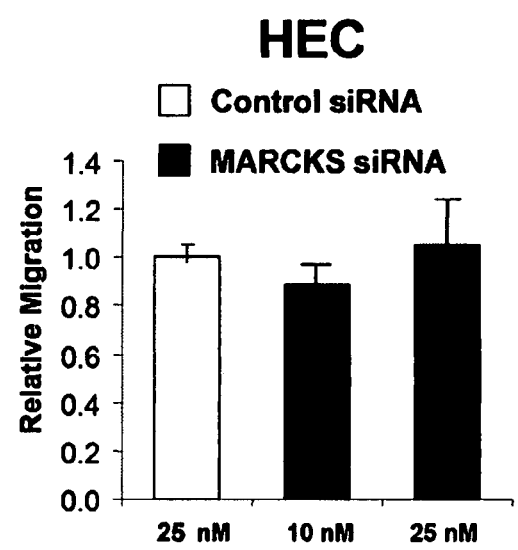
FIG. 14B is a bar graph depicting no significant difference in cellular migration of HECs after transfection with either 25 nM control siRNA (white bar), 10 nM MARCKS siRNA, or 25 nM MARCKS siRNA (black bars), indicating that MARCKS gene silencing does not affect cellular migration of HECs.
Figure 15A:
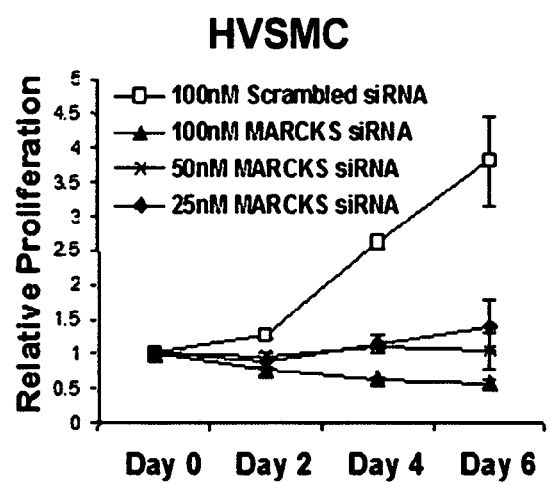
FIG. 15A is a graph depicting near complete arrest of HVSMC proliferation upon MARCKS silencing after transfection with MARCKS siRNA at 25, 50 and 100 nM concentrations, relative to 100 nM control scrambled siRNA.
Figure 15B:
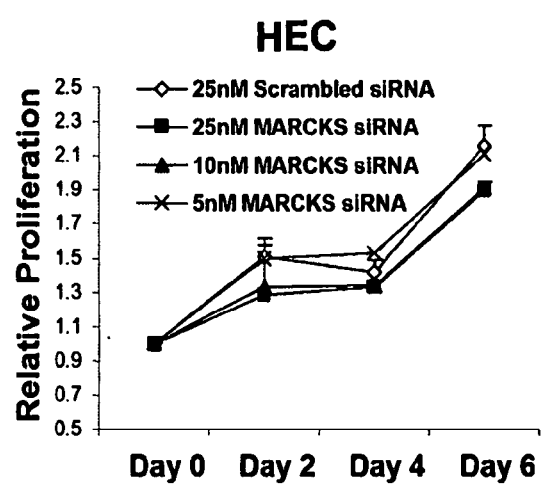
FIG. 15B is a graph depicting the proliferation of HECs after transfection with MARCKS siRNA at 5, 10 and 25 nM concentrations or 25 nM control scrambled siRNA. Full MARCKS knockdown following transfection with 25 nm MARCKS siRNA had only a minimal effect on HEC proliferation.

In HVSMCs, MARCKS silencing with 100 nM MARCKS siRNA reduced cellular migration to 68±7% (P=0.05) of controls (FIG. 14A). In HECs, MARCKS silencing with 25 nM MARCKS siRNA had no significant effect on cellular migration compared to controls (1.0±0.7 vs. 1.08±0.26, P=NS; FIG. 14B). The differential response of the two cell types was even more striking when assessing cellular proliferation. Here, even slight reductions in MARCKS mRNA levels in HVSMCs using 25 nM MARCKS siRNA led to a near complete arrest in HVSMC proliferation (1.41±0.36-fold increase vs. 3.82±0.65-fold increase for controls at day 6, P=0.005; FIG. 15A), whereas full MARCKS knockdown in HECs with 25 nM MARCKS siRNA had only a minimal effect on HEC proliferation (1.90±0.06-fold increase vs. 2.15±0.12-fold increase for controls at day 6, P=0.03; FIG. 15B). FACS analysis of HVSMCs after MARCKS knockdown confirmed a true arrest in cell cycle progression not related to increased cell death or apoptosis (data not shown).

Figures 16A, 16B:
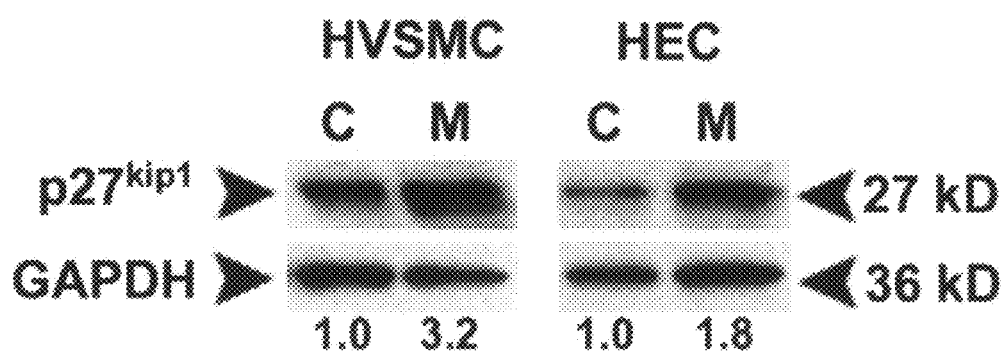
FIG. 16A is a Western blot depicting increased $p27^{kip1}$ protein levels in HVSMCs after transfection with 25 mM MARCKS (M) siRNA relative to HVSMCs transfected with 25 nM control (C) siRNA. GAPDH levels were used for corrected densitometry. MARCKS knockdown resulted in a 3.2 fold increase in $p27^{kip1}$ protein expression relative to controls.
FIG. 16B is a Western blot depicting increased $p27^{kip1}$ protein levels in HECs after transfection with 25 nM MARCKS (M) siRNA relative to HECs transfected with 25 nM control (C) siRNA. GAPDH levels were used for corrected densitometry. MARCKS knockdown resulted in a 1.8 fold increase in $p27^{kip1}$ protein expression relative to controls.

$p27^{kip1}$ is a cell cycle inhibitor that plays a role in regulating cellular proliferation in a diverse array of cell types, and has recently been shown to be important in promoting a quiescent differentiated VSMC phenotype in vitro (Izzard, T D et al. (2002) *Cardiovasc. Res.* 53(1):242-252; Castro, C. et al. (2003) *J. Biol. Chem.* 278(7):4482-4490) and in vivo (Abid, M R et al. (2005) *J. Biol. Chem.* 280(33):29864-29873). Quantitative comparison of $p27^{kip1}$ protein levels after GAPDH corrected densitometry revealed a 3.2-fold increase in $p27^{kip1}$ expression in HVSMCs after MARCKS knockdown compared to control cells (FIG. 16A) and only a 1.8-fold increase over controls in HECs (FIG. 16B). These results suggest involvement of $p27^{kip1}$ in reverting HVSMCs to the quiescent cell phenotype after MARCKS knockdown, yet also mirror the apparent phenotypic resistance of HECs to MARCKS knockdown, as this cell cycle inhibitor is only up-regulated in HECs to a fraction of the degree observed in HVSMCs. The effects of MARCKS knockdown in vascular cells has uncovered novel information about the divergent contributions of the MARCKS protein to VSMC and EC phenotypes, and revealed the powerful therapeutic potential for MARCKS as a gene target for siRNA silencing in vein grafts.

Example 8 siRNA-Mediated silencing of Multiple Gene Targets In Vitro

Materials and Methods
Cell Culture

Human coronary artery smooth muscle cells and endothelial cells (HCASMCs/HCAECs) were purchased from Cambrex (Walkersville, Md.) and cultured in smooth muscle cell (SmGM-2 BulletKit; Cambrex) or endothelial cell (EGM-2 BulletKit; Cambrex) media as per manufacturer's recommendations. All experiments were performed between passages 5 and 8 for both cell types.
siRNA Design siRNA targeting the housekeeping gene glyceraldehyde 3-phosphate dehydrogenase (GAPDH) was purchased from Ambion (Austin, Tex.). All other siRNAs were purchased from Dharmacon (Lafayette, Colo.). Additional siRNAs were designed to target the TNF-a receptor 1 (TNFRSF1A siGENOME duplex 2) the myristoylated alanine-rich C kinase substrate (MARCKS siGENOME duplex 4), and OB-cadherin (CDH11 siGENOME SMARTpool reagent). A single siRNA sequence that targets the MARCKS transcript has been used, (5'-GGU-GCC-CAG-UUC-UCC-AAG-AUU-3' [sense] (SEQ ID NO. 18), 5'-UCU-UGG-AGA-ACU-GGG-CAC-CUU-3' [anti-sense] (SEQ ID NO. 19)). The anti-sense strand is additionally modified with a phosphate group at the 5' end. Non-targeting control siRNA (sense 5'-CGC ACC AGA ACA AAC ACA C-3' (SEQ ID NO. 5)); Willis, D J et al. (2004) *Journal of Surgical Research* 120:27-36) was custom synthesized with dTdT overhangs on the 3' ends of both strands. Cy5-siRNA was synthesized by adding a 5'-Cy5 modification to the sense strand of the non-targeting control siRNA.
siRNA Lipofection Lipofection of HCASMCs and HCAECs was performed using the DharmAFECT1 transfection reagent (Dharmacon) for 24 hours in serum- and antibiotic-free media as per manufacturer's protocol.
Evaluation of siRNA Delivery After Lipofection Evaluation of siRNA delivery to HCASMCs and HCAECs after lipofection with 100 nM Cy5-siRNA was performed by confocal microscopy and fluorescence-activated cell sorter (FACS) analysis. For confocal microscopy, cells were plated on 2-well glass chamber slides (Nalge Nunc International, Rochester, N.Y.) at a density of 6,000 cells/cm$^2$ and lipofected with 100 nM Cy5-siRNA. 24 hours after the initiation of lipofection slides were washed twice with PBS and mounted using VECTASHIELD Mounting Medium (Vector Laboratories, Burlingame, Calif.). Three random high-power fields (20× objective) per slide were acquired using confocal microscopy and the number of cells demonstrating fluorescence was evaluated qualitatively. For FACS analysis, cells were seeded in 6-well plates at a density of 100,000 cells per well. 24 hours after the initiation of lipofection, cells were washed twice with PBS, recovered, fixed in 0.01% paraformaldehyde and processed to evaluate mean fluorescence.
Evaluation of mRNA Knockdown Evaluation of target gene mRNA knockdown after siRNA delivery was analyzed using a Stratagene MX3000P real time PCR (qRT-PCR) machine (Stratagene, La Jolla, Calif.). Total RNA was extracted from plate wells using RNeasy spin columns (Qiagen, Valencia, Calif.) and cDNA was prepared from 1 μl RNA using the iScript cDNA synthesis kit (Bio-Rad, Hercules, Calif.) prior to thermal cycling. For quantitative analysis, target gene levels were normalized to 18s or B₂M levels as previously described (Bustin, S A et al. (2004) *J. Mol. Endocrinol.* 29(1):23-39), and target and housekeeper gene amplification reactions were performed in triplicate for each cDNA sample using 1 μl cDNA per reaction. Target gene amplification was performed using Brilliant SYBR Green QPCR Reagent (Stratagene) and housekeeper gene amplification was performed in separate wells using Brilliant QPCR Master Mix (Stratagene) with gene-specific dual-labeled linear probes (IDT, Coralville, Iowa). Primer sequences, probe sequences, and final oligonucleotide concentrations used are as follows:

ern blotting with the use of standard techniques. Antibodies used for protein detection were: mouse monoclonal anti-GAPDH (1:10,000 dilution, Ambion), goat polyclonal anti-MARCKS (N-19) IgG (1:100 dilution, Santa Cruz Biotechnology, Santa Cruz, Calif.), mouse monoclonal anti-CDH11 (1:250 dilution, Abcam, Cambridge, Mass.), and mouse anti-β-tubulin IgM (clone 5H11 (1:250 dilution, Pharmingen, San Diego, Calif.). Secondary antibodies used were peroxidase-conjugated goat anti-mouse IgG (H+L) (1:1,000-1:5,000 dilution, Chemicon International, Temecula, Calif.) and peroxidase-conjugated rabbit anti-goat IgG (H+L) (1:500 dilu-

| Gene | Primer/Probe Sequences | Concentration (nM) |
|---|---|---|
| GAPDH | (f) 5'- AGT CAG CCG CAT CTT CTT TTG - 3' (SEQ ID NO. 6) | 300 |
| | (r) 5'- CGC CCA ATA CGA CCA AAT CC - 3' (SEQ ID NO. 7) | 300 |
| TNFRS1A | (f) 5'- CCT TTT ATC CCT CCT CTT CAT TGG - 3' (SEQ ID NO. 8) | 300 |
| | (r) 5'- GTG TCG ATT TCC CAC AAA CAA TG - 3' (SEQ ID NO. 9) | 300 |
| MARCKS | (f) 5'- CGG CAG AGT AAA AGA GCA AGC - 3' (SEQ ID NO. 16) | 300 |
| | (r) 5'- GGT TGT AGA CAA GTT CTC CAA AAC - 3' (SEQ ID NO. 17) | 300 |
| CDH11 | (f) 5'- CCC CGC AAA GAC ATC AAA CC - 3' (SEQ ID NO. 20) | 300 |
| | (r) 5'- TGT TGA TGA AGT CAT CGA CAT CC - 3' (SEQ ID NO. 21) | 300 |
| 18s | (f) 5'- GTT GAT TAA GTC CCT GCC CTT TG - 3' (SEQ ID NO. 10) | 30 |
| | (r) 5'- TAG TCA AGT TCG ACC GTC TTC TC -3' (SEQ ID NO. 11) | 30 |
| | Probe: 5'- Hex/CAC ACC GCC CGT CGC TAC TAC CG/IABlkFQ - 3' (SEQ ID NO. 12) | 100 |
| B₂M | (f) 5'- CTC CAC AGG TAG CTC TAG GAG - 3' (SEQ ID NO. 13) | 300 |
| | (r) 5'- TCT GAC CAA GAT GTT GAT GTT GG - 3' (SEQ ID NO. 14) | 300 |
| | Probe: 5'- Hex/TCT CTG CTC CCC ACC TCT AAG TTG CCA/IABlkFQ - 3' (SEQ ID NO. 15) | 300 |

Figure 17A:
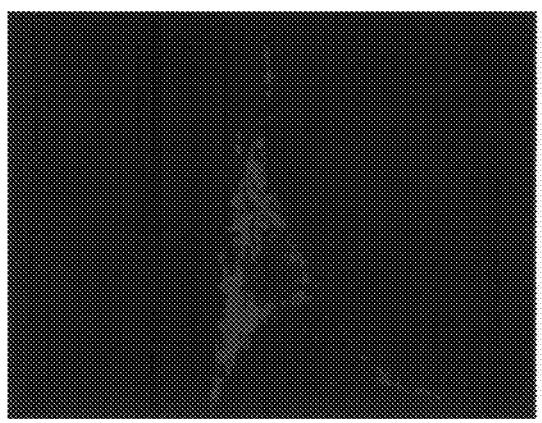
FIG. 17A is a representative confocal micrograph at 600× magnification of HCASMCs 24 hours after lipofection with 100 nM Cy5-siRNA demonstrating a characteristic pattern of granular perinuclear siRNA uptake.
Figure 17B:
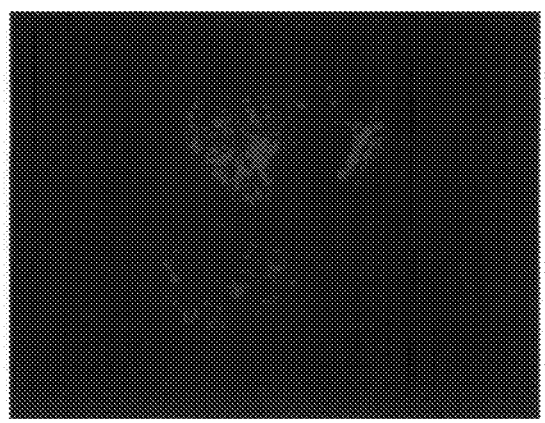
FIG. 17B is a representative confocal micrograph at 600× magnification of HCAECs 24 hours after lipofection with 100 nM Cy5-siRNA demonstrating a characteristic pattern of granular perinuclear siRNA uptake.
Figure 18A:
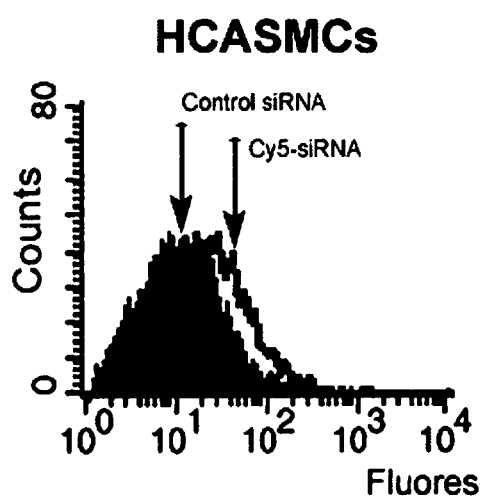
FIG. 18A depicts a quantitative FACS analysis of cell fluorescence in HCASMCs 24 hours after lipofection with either 100 nM control or Cy5-siRNA.
Figure 18B:
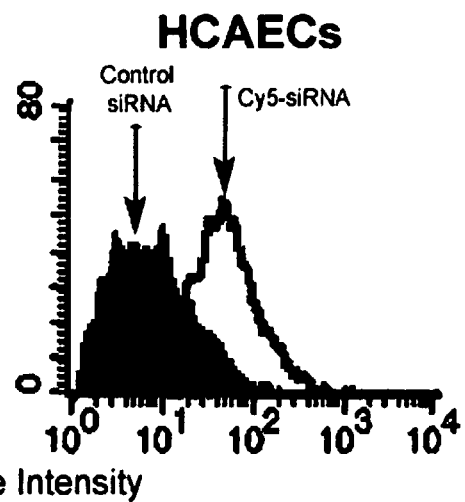
FIG. 18B depicts a quantitative FACS analysis of cell fluorescence in HCAECs 24 hours after lipofection with either 100 nM control or Cy5-siRNA demonstrating a 6.3-fold greater shift in mean fluorescence in HCAECs compared to HCASMCs (FIG. 18A; P<0.002). This result is indicates that HCAECs had taken up a larger total quantity of siRNA than HCASMCs.
Figure 19:
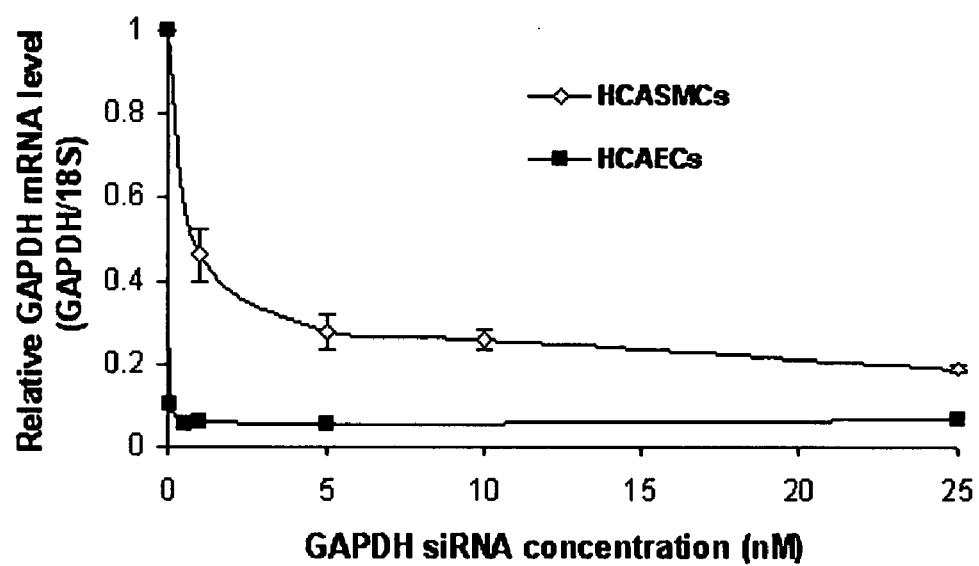
FIG. 19 is a graph depicting dose-response relationships for RNAi-mediated GAPDH mRNA knockdown 24 hours after lipofection with GAPDH siRNA demonstrating that significant mRNA knockdown in both cell types, with heightened knockdown in HCAECs at lower siRNA concentrations. GAPDH mRNA knockdown levels were calculated in comparison to GAPDH levels in cells lipofected with equal concentrations of non-targeting control siRNA.

Thermal cycling was performed under the following conditions: Stage 1: 10 minutes at 95° C.; Stage 2 (40 cycles): 30 seconds at 95° C., 1 minute at 60° C., 30 seconds at 72° C. The Comparative Quantification software tool was used to compare normalized gene levels from cells transfected with targeting siRNA vs. non-targeting control siRNA (calibrators). Plate-specific standard curves were generated for both target and housekeeper gene amplification reactions and used to calibrate the Comparative Quantification software tool.
Evaluation of Protein Knockdown Cell extracts were recovered from 6-well plates after siRNA lipofection and analyzed by sodium dodecyl sulfate-polyacrylamide gel electrophoresis (SDS-PAGE) and Westtion, Bio-Rad). Densitometry was performed using Adobe Photoshop 6.0 or NIH Image J 1.34.
Statistical Methods All experiments were performed in triplicate unless otherwise noted. Data are presented as means with standard deviation. Statistical analysis was performed using STATA software (STATA Corporation). Significance of association was assessed using the two-tailed Student t test (unpaired) or linear regression where appropriate.
Results HCASMCs and HCAECs demonstrated a characteristic pattern of granular perinuclear siRNA uptake in greater than 90% of cells of both cell types 24 hours after lipofection with 100 nM Cy5-siRNA (FIGS. 17A, 17B). Quantitative FACS analysis of cell fluorescence in these cells demonstrated a 6.3-fold greater shift in mean fluorescence in HCAECs (FIG. 18B) compared to HCASMCs (FIG. 18A; P<0.002), indicating a larger total quantity of siRNA uptake in HCAECs.

siRNA-mediated GAPDH mRNA knockdown 24 hours after lipofection with GAPDH siRNA resulted in significant mRNA knockdown in both cell types, with heightened knockdown in HCAECs at lower siRNA concentrations (FIG. 19).

Figure 20A:
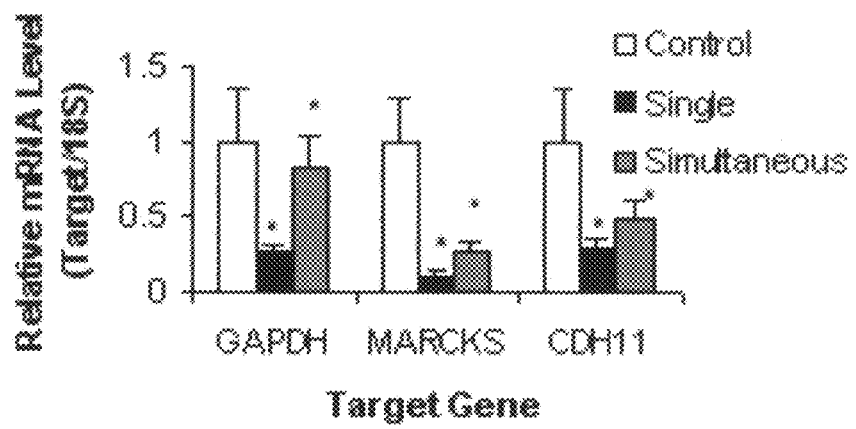
FIG. 20A is a bar graph depicting multi-gene silencing in HCASMCs. Relative mRNA knockdown levels are shown at 24 hours after lipofection with either 100 nM GAPDH, MARCKS, or CDH11 siRNA alone (black bars), or simultaneously with a 300 nM siRNA cocktail containing 100 nM of each of the 3 siRNA sequences (gray bars). mRNA knockdown levels are standardized to mRNA levels from cells lipofected with 300 nM non-targeting control siRNA (white bars). Statistically significant reductions in target gene mRNA levels (* denotes P<0.05) were observed in both cell types after single or simultaneous delivery of the three siRNAs.
Figure 20B:
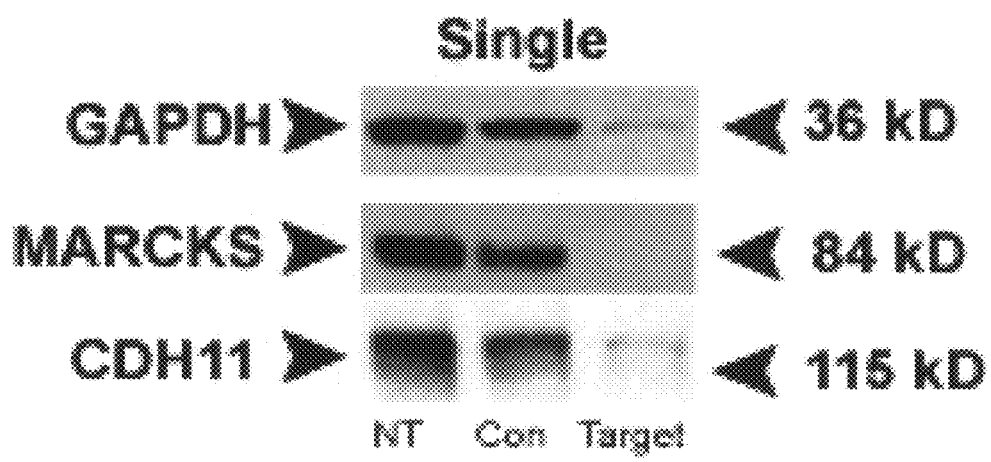
FIG. 20B is a Western blot on extracts from HCASMCs harvested 3-5 days after lipofection confirming gene knockdown at the protein level in cells transfected with target siRNA (Target), relative to untreated cells (NT) or cells transfected with 300 nM control siRNA (Con). The siRNA targets are indicated to the left of each panel (GAPDH, MARCKS, CDH11).
Figure 21A:
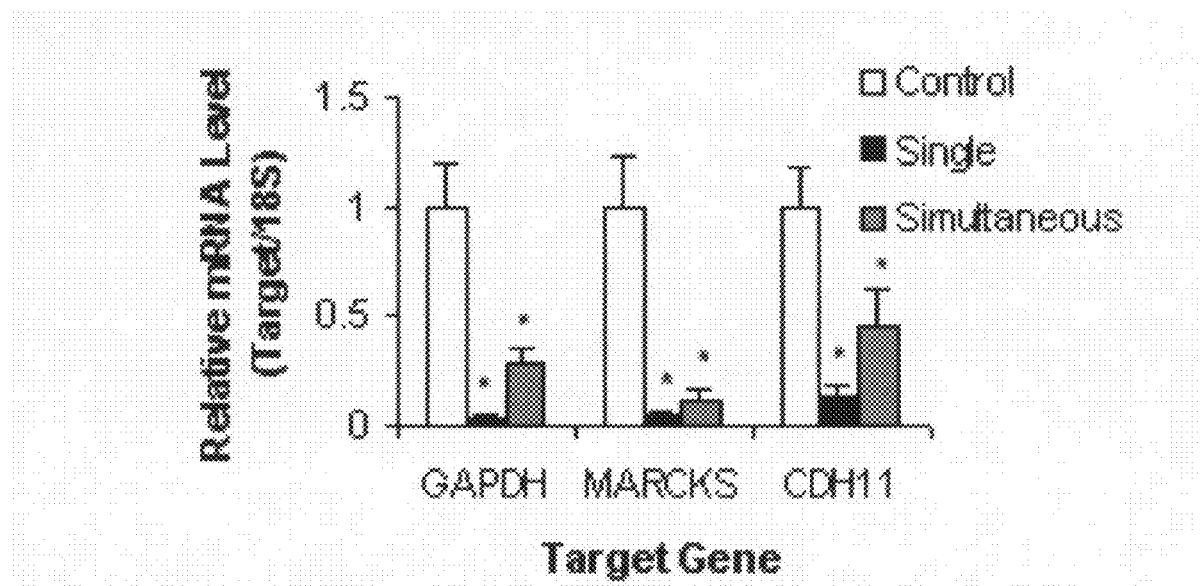
FIG. 21A is a bar graph depicting multi-gene silencing in HCAECs. Relative mRNA knockdown levels are shown at 24 hours after lipofection with either 100 nM GAPDH, MARCKS, or CDH11 siRNA alone (black bars), or simultaneously with a 300 nM siRNA cocktail containing 100 nM of each of the 3 siRNA sequences (gray bars). mRNA knockdown levels are standardized to mRNA levels from cells lipofected with 300 nM non-targeting control siRNA (white bars). Statistically significant reductions in target gene mRNA levels (* denotes P<0.05) were observed in both cell types after single or simultaneous delivery of the three siRNAs.
Figure 21B:
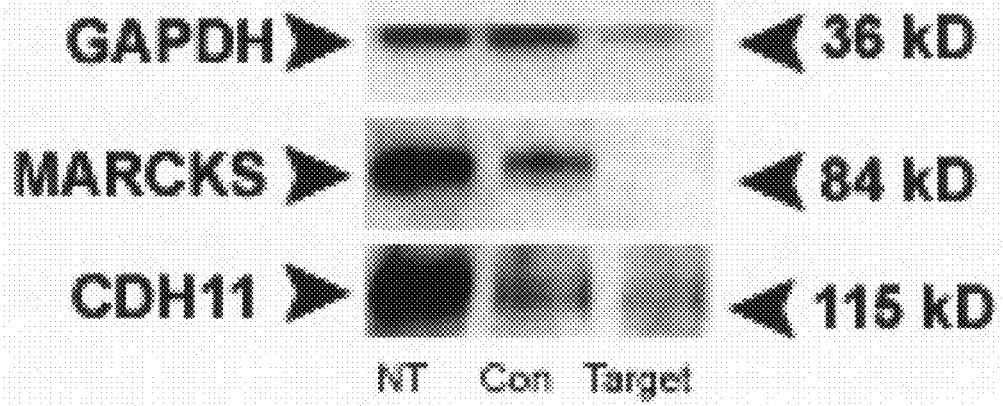
FIG. 21B is a Western blot on extracts from HCAECs harvested 3-5 days after lipofection confirming gene knockdown at the protein level in cells transfected with target siRNA (Target), relative to untreated cells (NT) or cells transfected with 300 nM control siRNA (Con). The siRNA targets are indicated to the left of each panel (GAPDH, MARCKS, CDH11).

To determine if HCASMCs and HCAECs are competent for multi-gene silencing using siRNA, mRNA knockdown levels were evaluated 24 hours after lipofection with a 300 nM siRNA cocktail containing of GAPDH, MARCKS, and CDH11 siRNAs, each at a 100 nM concentration, and were standardized to mRNA levels in cells transfected with 300 nM control siRNA. For comparison, mRNA knockdown levels were also measured in each cell type after lipofection singly with 100 nM of each of the three siRNAs.

mRNA levels of all three targets were successfully reduced in each cell type after transfection with the 3-gene cocktail (FIGS. 20A, 21A). In HCASMCs, mRNA levels were reduced by an average of 77±11% (P=0.0002) for single-gene siRNA lipofections and 46±28% (P=0.05) when lipofected with the three-gene cocktail (FIGS. 20A, 20B). In HCAECs, greater mRNA knockdown was achieved, reaching 93±5% (P=0.0001) and 72±18% (P=0.002) respectively (FIG. 21A). Corresponding Western blots from cells harvested 3-5 days after lipofection confirm gene knockdown at the protein level when compared to untreated cells or cells transfected with 300 nM control siRNA (FIGS. 20B, 21B).

These data indicate that both vascular cell types are competent for multi-gene silencing of at least three targets using three different siRNAs. However, the knockdown effect appears to be somewhat compromised as when multiple targets are silenced suggesting a modest limit to the number of siRNAs that can be used in unison. HCAECs appear to be more susceptible to siRNA-mediated gene silencing than HCASMCs in vitro. If true in whole vein grafts, this difference in siRNA susceptibility could be exploited therapeutically to differentially affect gene expression in the two tissue layers by including siRNAs at low dose that afford phenotypic protection to HCAECs without affecting gene expression in HCASMCs.

Example 9

Rapid siRNA Transfection of Vascular Cells with MARCKS siRNA In Vitro

Materials and Methods
Cell Culture

Human coronary artery smooth muscle cells and endothelial cells (HCASMCs/HCAECs) were purchased from Cambrex (Walkersville, Md.) and cultured in smooth muscle cell (SmGM-2 BulletKit; Cambrex) or endothelial cell (EGM-2 BulletKit; Cambrex) media as per manufacturer's recommendations. All experiments were performed between passages 5 and 8 for both cell types.

siRNA Design siRNA targeting the housekeeping gene glyceraldehyde 3-phosphate dehydrogenase (GAPDH) was purchased from Ambion (Austin, Tex.). All other siRNAs were purchased from Dharmacon (Lafayette, Colo.). Additional siRNAs were designed to target the TNF-α receptor 1 (TNFRSF1A siGENOME duplex 2) and MARCKS. A single siRNA sequence that targets the MARCKS transcript has been used, (5'-GGU-GCC-CAG-UUC-UCC-AAG-AUU-3' [sense] (SEQ ID NO. 18), 5'-UCU-UGG-AGA-ACU-GGG-CAC-CUU-3' [antisense] (SEQ ID NO. 19)). The anti-sense strand is additionally modified with a phosphate group at the 5' end. Non-targeting control siRNA (sense 5'-CGC ACC AGA ACA AAC ACA C-3' (SEQ ID NO. 5); Willis, DJ et al. (2004) *Journal of Surgical Research* 120:27-36) was custom synthesized with dTdT overhangs on the 3' ends of both strands. Cy5-siRNA was synthesized by adding a 5'-Cy5 modification to the sense strand of the non-targeting control siRNA.

Rapid siRNA Transfection

To more rigorously study the effects of pressure on gene silencing in vascular cells and develop an in vitro model for rapid siRNA transfection, a chamber that could hold standard tissue culture plates and be pressurized with wall air was fabricated. HVSMCs and HECs were seeded in 96-well plates at a density of 6,000 cells/cm$^2$ and were treated with Control or MARCKS siRNA suspended in normal saline solution, without the addition of a transfection reagent, at concentrations from 1-25 μM in either water, lactate ringers solution (Baxter, Deerfield, Ill.), normal saline (Baxter), cell media, or Plasmalyte A (Baxter) supplemented with 12 mg/ml papaverine hydrochloride and 4 units/ml heparin sodium (LoGerfo, FW et al. (1984) *Arch. Surg.* 119(10): 1212-1214). First, siRNA solutions were applied to one plate of each cell type and rapid siRNA transfection was performed by placing cells in the specially-designed pressure chamber for 10 minutes while raising the ambient pressure by 0-1 ATM using wall air. Cells were then removed from the chamber and the siRNA solution was promptly aspirated and replaced with fresh media prior to returning the plates to the incubator. Parallel plates were subjected the same siRNA treatment and placed in the chamber for 10 minutes without pressurization.

Evaluation of siRNA Delivery After Rapid Transfection

Evaluation of siRNA delivery after rapid siRNA transfection with Cy5-siRNA was performed using confocal microscopy and FACS analysis. For confocal microscopy, cells were plated on 2-well glass chamber slides (Nalge Nunc International, Rochester, N.Y.) at a density of 6,000 cells/cm$^2$ and transfected for 10 minutes with 25 μM Cy5-siRNA suspended in normal saline using the rapid transfection technique with pressures up to 0.4 ATM above ambient pressure. 24 hours after transfection slides were washed twice with PBS and mounted using VECTASHIELD Mounting Medium (Vector Laboratories, Burlingame, Calif.). Two random high-power fields (20× objective) per slide were acquired using confocal microscopy and the amount of Cy5 fluorescence per imaged cell was quantified using Adobe PhotoShop 6.0. For FACS analysis, cells were seeded in 6-well plates at a density of 6,000 cells/cm$^2$ and transfected for 10 minutes with 5 μM Cy5-siRNA suspended in cell media using the rapid transfection technique with pressures up to 0.4 ATM above ambient pressure. 24 hours after transfection, cells were washed twice with PBS, recovered, fixed in 0.01% paraformaldehyde and processed by FACS analysis to evaluate mean fluorescence.

Evaluation of mRNA Knockdown

Evaluation of target gene mRNA knockdown was performed as described in Example 8 above.

Statistical Methods

All experiments were performed in triplicate unless otherwise noted. Data are presented as means with standard deviation. Statistical analysis was performed using STATA software (STATA Corporation). Significance of association was assessed using the two-tailed Student t test (unpaired) or linear regression where appropriate.

Results

Non-distending pressure transfection has been shown by Mann et al. and others to increase total oligodeoxynucleotide (ODN) uptake by human vein (Mann, M J et al. (1999) *Proc. Natl. Acad. Sci. USA* 96(11):6411-6416; Shintani, T. et al. (2002) *Ann. Thorac. Surg.* 74(4):1132-1137). However, given that this technique does not establish a hydrodynamic pressure gradient for diffusion across the vessel wall, it was hypothesized that the efficacy of this method might be related to changes in membrane dynamics or intracellular processes of ODN trafficking that are enhanced by exposure to pressure.

Figure 22:
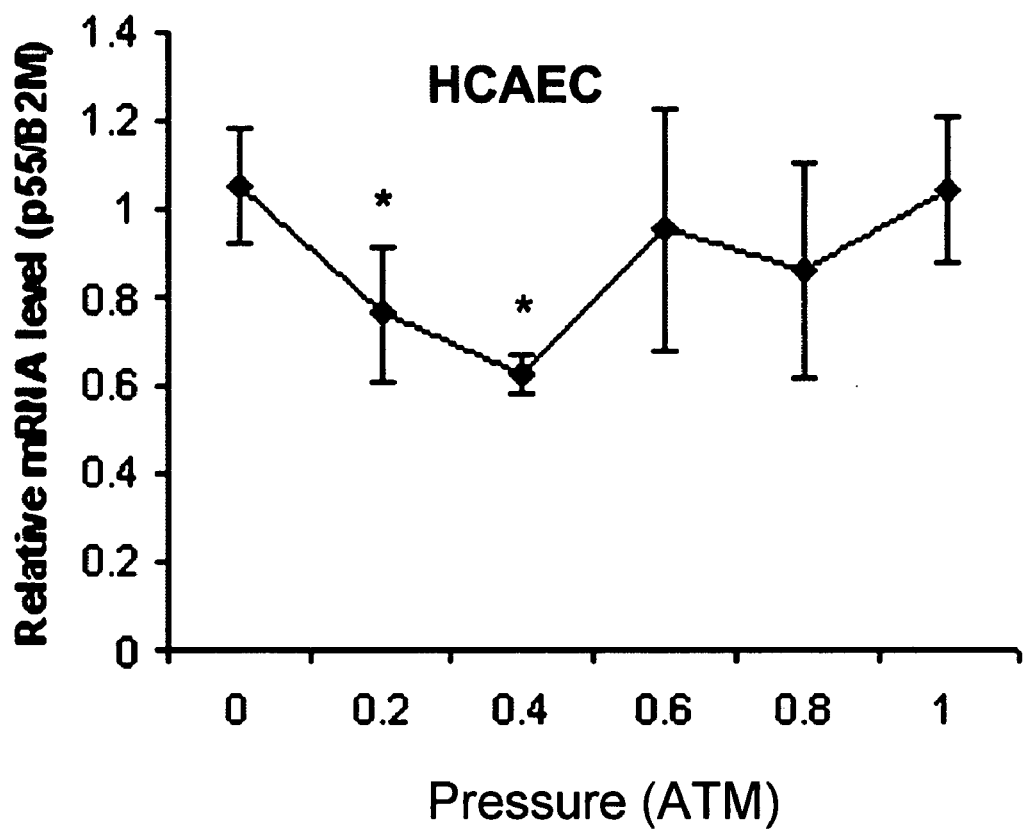
FIG. 22 is a graph depicting a pressure-response curve for cells harvested 24 hours after rapid 10 minute transfection with p55 siRNA demonstrating optimal gene knockdown when siRNA transfection is performed using 0.4 ATM increased ambient pressure (* denotes P<0.05). This affect is diminished when transfection is performed using higher pressures. p55 mRNA knockdown values were measured relative to cells that were transfected in parallel with non-targeting control siRNA.

A pressure-response curve (FIG. 22) for cells harvested 24 hours after rapid 10 minute transfection with TNF-α receptor 1 (TNFRSF1A/p55) siRNA demonstrated optimal gene knockdown when using 0.4 ATM increased ambient pressure (* denotes P<0.05). This affect is diminished when using higher pressures. TNFRSF1A/p55 mRNA knockdown values are compared to cells transfected in parallel with non-targeting control siRNA. Further optimization of gene knockdown after rapid siRNA transfection was performed by resuspending TNFRSF1A/p55 siRNA in a variety of solutions (Table 2). The solution that was used affected knockdown levels, with balanced physiologic solutions leading to the greatest degree of TNFRSF1A/p55 mRNA knockdown (Table 2).

Figures 23A, 23B:
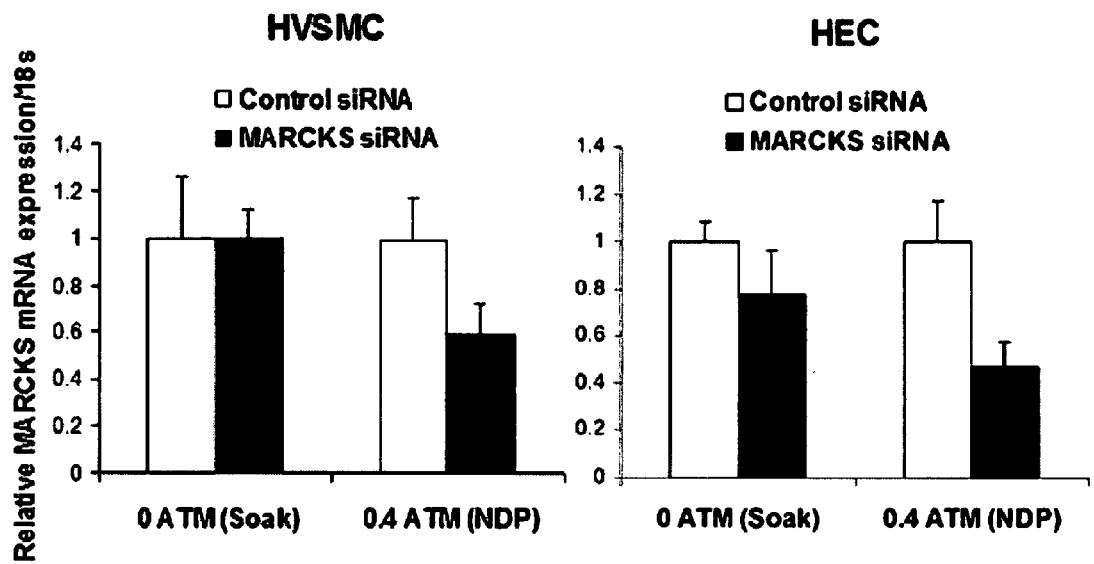
FIG. 23A is a bar graph depicting the results of qRT-PCR analysis showing MARCKS mRNA knockdown levels in HVSMCs 24 hours post-transfection with siRNA by either soaking the cells in siRNA solution (Soak) or using 0.4 ATM of non-distending pressure (NDP). MARCKS mRNA knockdown levels in cells transfected with MARCKS siRNA (black bars) are shown relative to MARCKS mRNA levels in cells that were transfected with non-targeting control siRNA (white bars).
FIG. 23B is a bar graph depicting the results of qRT-PCR analysis showing MARCKS mRNA knockdown levels in HECs 24 hours post-transfection with siRNA by either soaking the cells in siRNA solution (Soak) or using 0.4 ATM of non-distending pressure (NDP). MARCKS mRNA knockdown levels in cells transfected with MARCKS siRNA (black bars) are shown relative to MARCKS mRNA levels in cells that were transfected with non-targeting control siRNA (white bars).

When cells were plated at low confluency (2000 cells per well) and transfected with MARCKS siRNA, the cells that were subjected to pressure treatment displayed substantial enhancement of MARCKS knockdown compared to cells treated with the siRNA solution in the absence of pressure (for HVSMCs (FIG. 23A), 0±12% MARCKS knockdown at 0 ATM vs. 41±12% knockdown at 0.4 ATM, P=0.02. For HECs (FIG. 23B), 22±17% MARCKS knockdown at 0 ATM vs. 53±10% at 0.4 ATM, P=0.03).

TABLE 2

Optimization of rapid siRNA transfection-mediated gene knockdown. Increased Ambient Pressure (ATM)

| Solution | p55 mRNA knockdown | P-value |
|---|---|---|
| HCASMC | | |
| Water | 28 ± 15% | 0.13 |
| Lactate Ringers | 17 ± 22% | NS |
| Normal Saine | | |
| SmBM cell media, 4° C. | 14 ± 10% | NS |
| SmBM cell media, 25° C. | 26 ± 5% | 0.04 |
| SmBM cell media, 37° C. | 27 ± 12% | 0.08 |
| SmBM cell media w/DharmaFECT1 | | |
| SmBM cell media w/SmGM-2 BulletKit Plasmalyte A w/Heparin/papavarine | 41 ± 13% | 0.02 |

TABLE 2-continued

Optimization of rapid siRNA transfection-mediated gene knockdown. Increased Ambient Pressure (ATM)

| Solution | p55 mRNA knockdown | P-value |
|---|---|---|
| HCAEC | | |
| Water | | |
| Lactate Ringers | 18 ± 9% | 0.03 |
| Normal Saline | 23 ± 5% | 0.03 |
| EBM-2 cell media, 4° C. | | |
| EBM-2 cell media, 25° C. | 36 ± 16% | 0.03 |
| EBM-2 cell media, 37° C. | | |
| EBM-2 cell media w/DharmaFECT1 | 39 ± 5% | 0.01 |
| EBM-2 cell media w/EGM-2MV Bullet-kit Plasmalyte A w/Heparain/papavarine | | |

Figure 24A:
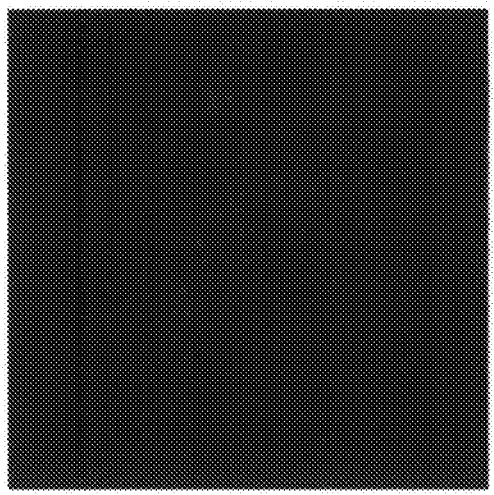
FIG. 24A is a representative fluorescent confocal micrograph at 600× magnification of HCASMCs that were fixed 24 hours after rapid siRNA transfection with 25 μM Cy5-siRNA at ambient pressure demonstrating siRNA uptake in these vascular cells.
Figure 24B:
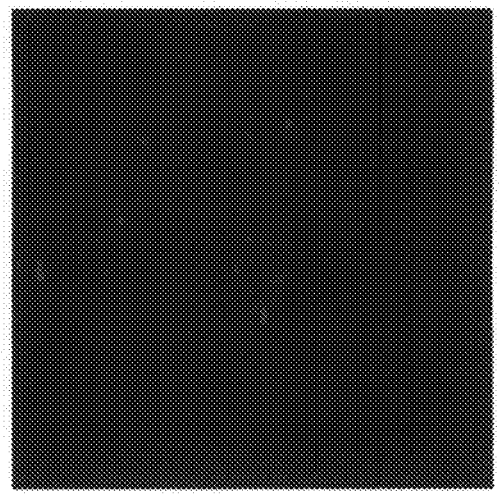
FIG. 24B is a representative fluorescent confocal micrograph at 600× magnification of HCAECs that were fixed 24 hours after rapid siRNA transfection with 25 μM Cy5-siRNA at ambient pressure demonstrating siRNA uptake in these vascular cells.
Figure 26A:
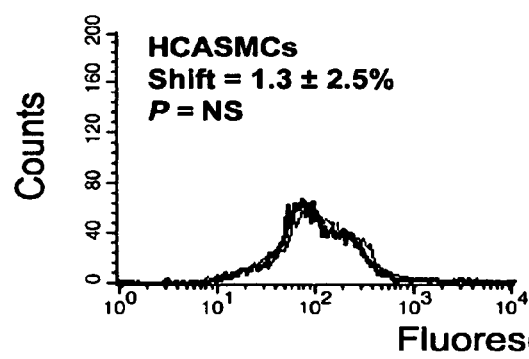
FIG. 26A depicts quantitative FACS analysis of HCASMCs 24 hours after a 10 minute pressure transfection at 0.4 ATM with Cy5-siRNA demonstrating no significant shift in mean fluorescence when compared to cells transfected with Cy5-siRNA at ambient pressure (N=2 for each group).
Figure 26B:
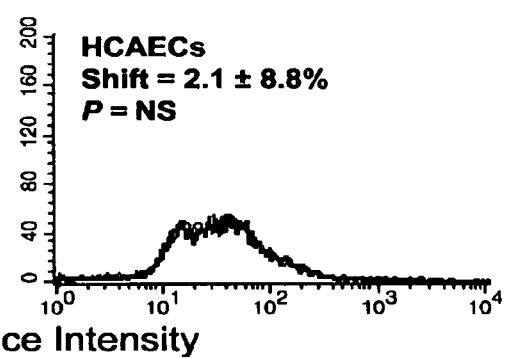
FIG. 26B depicts quantitative FACS analysis of HCAECs 24 hours after a 10 minute pressure transfection at 0.4 ATM with Cy5-siRNA demonstrating no significant shift in mean fluorescence when compared to cells transfected with Cy5-siRNA at ambient pressure (N=2 for each group).

Analysis of HCASMCs and HCAECs fixed 24 hours after rapid siRNA transfection with 25 µM Cy5-siRNA at ambient pressure using confocal microscopy demonstrated siRNA uptake in cells of both types (FIGS. 24A, 24B). Quantitation of cell fluorescence revealed that fluorescence did not increase as the transfecting pressure was raised (FIGS. 25A, 25B; n is listed above the bar graph for each treatment and equals the number of cells quantitated. * denotes P<0.05). Quantitative FACS analysis of HCASMCs (FIG. 26A) and HCAECs (FIG. 26B) 24 hours after a 10 minute pressure transfection at 0.4 ATM with Cy5-siRNA produced no significant shift in mean fluorescence when compared to cells transfected with Cy5-siRNA at ambient pressure (N=2 for each group). Therefore, our results demonstrated no significant shift in mean fluorescence for either cell type after the application of pressure.

Together, these data show that pressure potentiates gene silencing in vitro without increasing siRNA delivery, suggesting a novel intracellular RNA interference mechanism in vascular cells that can be manipulated through the application of pressure. Furthermore, these results demonstrate at the cellular level that vascular cells are competent for rapid siRNA transfection and gene silencing after only 10 minutes of exposure to siRNA and establish an in vitro model for rapid siRNA transfection that can be used to test and optimize conditions for increasing the strength of gene silencing after rapid siRNA application.

The relevant teachings of all publications cited herein that have not explicitly been incorporated by reference, are incorporated herein by reference in their entirety. One skilled in the art will readily appreciate that the present invention is well adapted to carry out the objects and obtain the ends and advantages mentioned, as well as those inherent therein. The present invention may be embodied in other specific forms without departing from the scope of the invention encompassed by the appended claims.

What is claimed is:

1. A method of inhibiting at least one vascular smooth muscle cell response selected from the group consisting of cell proliferation and cell migration, the method comprising transfecting vascular smooth muscle cells with a nucleic acid molecule that comprises a nucleotide sequence that is at least 90% homologous to a portion of SEQ ID NO: 3, wherein said nucleic acid molecule hybridizes to SEQ ID NO: 3 and inhibits expression of a myristolated alanine-rich C kinase substrate (MARCKS) protein having the amino acid sequence of SEQ ID NO: 4 in said cells, wherein the nucleic acid molecule is about 17 nucleotides to about 29 nucleotides in length.

2. The method of claim 1, wherein the smooth muscle cell response is cell proliferation.

3. The method of claim 1, wherein the smooth muscle cell response is cell migration.

4. The method of claim 1, wherein the nucleic acid molecule induces post-transcriptional silencing of at least one gene encoding the MARCKS.

5. The method of claim 1, wherein the nucleic acid molecule comprises RNA.

6. The method of claim 5, wherein the RNA is small interfering RNA (siRNA).

7. The method of claim 1, wherein the vascular smooth muscle cells are present in a vein graft.

8. The method of claim 1, wherein the vascular smooth muscle cells are human vascular smooth muscle cells.

9. The method of claim 5, wherein the RNA is double-stranded.

10. A method of inhibiting expression of one or more genes encoding a MARCKS protein having the amino acid sequence of SEQ ID NO: 4 in a vascular smooth muscle cell, the method comprising transfecting said vascular smooth muscle cell with a nucleic acid molecule that comprises a nucleotide sequence that is at least 90% homologous to a portion of SEQ ID NO: 3, wherein said nucleic acid molecule hybridizes to SEQ ID NO: 3 and induces post-transcriptional silencing of said one or more genes, wherein the nucleic acid molecule is about 17 nucleotides to about 29 nucleotides in length.

11. The method of claim 10, wherein the nucleic acid molecule comprises RNA.

12. The method of claim 11, wherein the RNA is double-stranded.

13. The method of claim 11, wherein the RNA is small interfering RNA (siRNA).

14. The method of claim 10, wherein the vascular smooth muscle cell is present in a vein graft.

15. The method of claim 10, wherein the vascular smooth muscle cell is a mammalian vascular smooth muscle cell.

16. The method of claim 15, wherein the vascular smooth muscle cell is a human vascular smooth muscle cell.

17. The method of claim 1, wherein the nucleic acid molecule comprises a nucleotide sequence that is 100% homologous to a portion of SEQ ID NO:3.

18. The method of claim 10, wherein the nucleic acid molecule comprises a nucleotide sequence that is 100% homologous to a portion of SEQ ID NO:3.

* * * * *

SEQUENCE LISTING

<160> NUMBER OF SEQ ID NOS: 21

<210> SEQ ID NO 1
<211> LENGTH: 1584
<212> TYPE: DNA
<213> ORGANISM: Homo sapiens

<400> SEQUENCE: 1

```
ggcattctgg cgcggagcgg agcggcggcg ggcgcagcta gcgggtcggc cgcggagcgg      60
aggtgcagct cggcttcccc cggcacccct cccactcggg cgccagcccc acccctcagc     120
cggccgggcc gaccacgccg tactatcccc tgcggcgcga gccgggggcg gctccaagcg     180
cccccccagca gaccccccatc atgggcagcc agagctccaa ggctcccccgg ggcgacgtga    240
ccgccgagga ggcagcaggc gcttcccccg cgaaggccaa cggccaggag aatggccacg     300
tgaaaagcaa tggagactta tcccccaagg gtgaaggga gtcgccccct gtgaacggaa     360
cagatgaggc agccggggcc actggcgatg ccatcgagcc agcacccact agccagggtg     420
ctgaggccaa gggggaggtc ccccccaagg agacccccaa gaagaagaag aaattctctt     480
tcaagaagcc tttcaaattg agcggcctgt ccttcaagag aaatcggaag gagggtgggg     540
gtgattcttc tgcctcctca cccacagagg aagagcagga gcaggggag atcggtgcct     600
gcagcgacga gggcactgct caggaaggga aggccgcagc caccctgag agccaggaac     660
cccaggccaa gggggcagag gctagtgcag cctcagaaga agaggcaggg ccccaggcta     720
cagagccatc cactccctcg gggccggaga gtggccctac accagccagc gctgagcaga     780
atgagtagct aggtaggggc aggtgggtga tctctaagct gcaaaaactg tgctgtcctt     840
gtgaggtcac tgcctggacc tggtgccctg gctgccttcc tgtgcccaga aggaagggg     900
ctattgcctc ctcccagcca cgttccgttt cctcctctcc ctcctgtgga ttctcccatc     960
agccatctgg ttctcctctt aaggccagtt gaagatggtc ccttacagct tcccaagtta    1020
ggttagtgat gtgaaatgct cctgtccctg gccctacctc cttccctgtc cccacccctg    1080
cataaggcag ttgttggttt tcttccccaa ttcttttcca gtaggtttt gtttacccta    1140
ctccccaaat ccctgagcca gaagtggggt gcttatactc ccaaaccttg agtgtccagc    1200
cttcccctgt tgtttttagt ctcttgtgct gtgcctagtg gcacctgggc tggggaggac    1260
actgccccgt ctaggttttt ataaatgtct tactcaagtt caaacctcca gcctgtgaat    1320
caactgtgtc tctttttga cttggtaagc aagtattagg ctttggggtg ggggaggtc    1380
tgtaatgtga acaacttct tgtcttttttt tctcccactg ttgtaaataa cttttaatgg    1440
ccaaacccca gatttgtact ttttttttttt ttctaactgc taaaaccatt ctcttccacc    1500
tggttttact gtaacatttg gaaaggaat aaatgtcgtc cctttaaaaa aaaaaaaaa    1560
aaaaaagaa aaaaaaaaa aaaa                                             1584
```

<210> SEQ ID NO 2
<211> LENGTH: 195
<212> TYPE: PRT
<213> ORGANISM: Homo sapiens

<400> SEQUENCE: 2

```
Met Gly Ser Gln Ser Ser Lys Ala Pro Arg Gly Asp Val Thr Ala Glu
  1               5                  10                  15

Glu Ala Ala Gly Ala Ser Pro Ala Lys Ala Asn Gly Gln Glu Asn Gly
             20                  25                  30

His Val Lys Ser Asn Gly Asp Leu Ser Pro Lys Gly Glu Gly Glu Ser
         35                  40                  45

Pro Pro Val Asn Gly Thr Asp Glu Ala Ala Gly Ala Thr Gly Asp Ala
     50                  55                  60

Ile Glu Pro Ala Pro Thr Ser Gln Gly Ala Glu Ala Lys Gly Glu Val
 65                  70                  75                  80
```

```
Pro Pro Lys Glu Thr Pro Lys Lys Lys Lys Phe Ser Phe Lys Lys
            85                  90                  95

Pro Phe Lys Leu Ser Gly Leu Ser Phe Lys Arg Asn Arg Lys Glu Gly
            100                 105                 110

Gly Gly Asp Ser Ser Ala Ser Ser Pro Thr Glu Glu Gln Glu Gln
            115                 120                 125

Gly Glu Ile Gly Ala Cys Ser Asp Glu Gly Thr Ala Gln Gly Lys
        130                 135                 140

Ala Ala Ala Thr Pro Glu Ser Gln Pro Gln Ala Lys Gly Ala Glu
145             150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195

<210> SEQ ID NO 3
<211> LENGTH: 2516
<212> TYPE: DNA
<213> ORGANISM: Homo sapiens

<400> SEQUENCE: 3 tcgactttc cacccttttt ccctcccctcc tgtgctgctg cttttgatc tcttcgacta      60 aaattttttt atccggagtg tatttaatcg gttctgttct gtcctctcca ccaccccac    120 cccctccct ccggtgtgtg tgccgctgcc gctgttgccg ccgccgctgc tgctgctgct    180
cgccccgtcg ttacaccaac ccgaggctct tgtttccccc tcttggatct gttgagtttc    240
tttgttgaag aagccagcat gggtgcccag ttctccaaga ccgcagcgaa gggagaagcc    300
gccgcggaga ggcctgggga ggcggctgtg gcctcgtcgc cttccaaagc gaacggacag    360
gagaatggcc acgtgaaggt aaacggcgac gcttcgcccg cggccgccga gtcgggcgcc    420
aaggaggagc tgcaggccaa cggcagcgcc ccggccgccg acaaggagga gcccgcggcc    480
gccgggagcg ggcggcgtc gccctccgcg gccgagaaag gtgagccggc cgccgccgct    540 gccccccagag ccgggggccag cccggtagag aaggaggccc ccgcggaagg cgaggctgcc    600
gagcccggct cgcccacggc cgcggaggga gaggccgcgt cggccgcctc ctcgacttct    660
tcgcccaagg ccgaggacgg ggccacgccc tcgcccagca acgagacccc gaaaaaaaaa    720
aagaagcgct tttccttcaa gaagtctttc aagctgagcg gcttctcctt caagaagaac    780
aagaaggagg ctggagaagg cggtgaggct gaggcgcccg ctgccgaagg cggcaaggac    840
gaggccgccg gggcgcagc tgcggccgcc gccgaggcgg gcgcggcctc cggggagcag    900
gcagcggcgc cgggcgagga ggcggcagcg ggcgaggagg gggcggcggg tggcgacccg    960
caggaggcca agccccagga ggcgctgtc gcgccagaga agccgcccgc cagcgacgag   1020
accaaggccg ccgaggagcc cagcaaggtg gaggagaaaa aggccgagga ggccggggcc   1080
agcgccgccg cctgcgaggc cccctccgcc gcggggcccg gcgcgccccc ggagcaggag   1140 gcagccccg cggaggagcc ccggccgcc gcagcctcgt cagcctgcgc agccccctca   1200
caggaggccc agcccgagtg cagtccagaa gccccccag cggaggcggc agagtaaaag   1260
agcaagcttt tgtgagataa tcgaagaact ttctccccc gtttgtttgt tggagtggtg   1320
ccaggtactg gttttggaga acttgtctac aaccagggat tgattttaaa gatgtctttt   1380 tttatttac tttttttaa gcaccaaatt ttgttgtttt ttttttctcc cctccccaca   1440
```

```
gatcccatct caaatcattc tgttaaccac cattccaaca ggtcgaggag agcttaaaca   1500
ccttcttcct ctgccttgtt tctctttttat tttttatttt ttcgcatcag tattaatgtt   1560
tttgcatact ttgcatcttt attcaaaagt gtaaactttc tttgtcaatc tatggacatg   1620
cccatatatg aaggagatgg gtgggtcaaa aagggatatc aaatgaagtg atagggggtca   1680 caatggggaa attgaagtgg tgcataacat tgccaaaata gtgtgccact agaaatggtg   1740
taaaggctgt cttttttttt ttttttttaaa gaaaagttat taccatgtat tttgtgaggc   1800
aggtttacaa cactacaagt cttgagttaa aaggaaaga ggaaaaaaga aaaacacca    1860 atacccagat ttaaaaaaaa aaaaacgatc atagtcttag gagttcattt aaaccatagg   1920
aacttttcac ttatctcatg ttagctgtac cagtcagtga ttaagtagaa ctacaagttg   1980
tataggcttt attgtttatt gctggtttat gaccttaata aagtgtaatt atgtattacc   2040
agcagggtgt ttttaactgt gactattgta taaaaacaaa tcttgatatc cagaagcaca   2100
tgaagtttgc aactttccac cctgcccatt tttgtaaaac tgcagtcatc ttggaccttt   2160
taaaacacaa attttaaact caaccaagct gtgataagtg gaatggttac tgtttatact   2220
gtggtatgtt tttgattaca gcagataatg ctttcttttc cagtcgtctt tgagaataaa   2280
ggaaaaaaaa atcttcagat gcaatggttt tgtgtagcat cttgtctatc atgttttgta   2340
aatactggag aagctttgac caatttgact tagagatgga atgtaacttt gcttacaaaa   2400
attgctatta aactcctgct taaggtgttc taattttctg tgagcacact aaaagcgaaa   2460
aataaatgtg aataaaatgt aaaaaaaaaa aaaaaaaaaa aaaaaaaaaa aaaaaa       2516
```

<210> SEQ ID NO 4
<211> LENGTH: 332
<212> TYPE: PRT
<213> ORGANISM: Homo sapiens

<400> SEQUENCE: 4

```
Met Gly Ala Gln Phe Ser Lys Thr Ala Ala Lys Gly Glu Ala Ala Ala
 1               5                  10                  15

Glu Arg Pro Gly Glu Ala Ala Val Ala Ser Ser Pro Ser Lys Ala Asn
             20                  25                  30

Gly Gln Glu Asn Gly His Val Lys Val Asn Gly Asp Ala Ser Pro Ala
         35                  40                  45

Ala Ala Glu Ser Gly Ala Lys Glu Glu Leu Gln Ala Asn Gly Ser Ala
     50                  55                  60

Pro Ala Ala Asp Lys Glu Glu Pro Ala Ala Gly Ser Gly Ala Ala
 65                  70                  75                  80

Ser Pro Ser Ala Ala Glu Lys Gly Glu Pro Ala Ala Ala Ala Pro
                 85                  90                  95

Glu Ala Gly Ala Ser Pro Val Glu Lys Glu Ala Pro Ala Glu Gly Glu
            100                 105                 110

Ala Ala Glu Pro Gly Ser Pro Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190
```

```
Lys Asp Glu Ala Ala Gly Gly Ala Ala Ala Ala Glu Ala Gly
            195                 200                 205

Ala Ala Ser Gly Glu Gln Ala Ala Pro Gly Glu Ala Ala Ala
    210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Gly Pro Gly
    275                 280                 285

Ala Pro Pro Glu Gln Glu Ala Ala Pro Ala Glu Glu Pro Ala Ala Ala
            290                 295                 300

Ala Ala Ser Ser Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
cgcaccagaa caaacacac                                          19

<210> SEQ ID NO 6
<211> LENGTH: 21
<212> TYPE: DNA
<213> ORGANISM: Artificial Sequence
<220> FEATURE:
<223> OTHER INFORMATION: primer sequence

<400> SEQUENCE: 6
agtcagccgc atcttctttt g                                       21

<210> SEQ ID NO 7
<211> LENGTH: 20
<212> TYPE: DNA
<213> ORGANISM: Artificial Sequence
<220> FEATURE:
<223> OTHER INFORMATION: primer sequence

<400> SEQUENCE: 7
cgcccaatac gaccaaatcc                                         20

<210> SEQ ID NO 8
<211> LENGTH: 24
<212> TYPE: DNA
<213> ORGANISM: Artificial Sequence
<220> FEATURE:
<223> OTHER INFORMATION: primer sequence

<400> SEQUENCE: 8 cctttatcc ctcctcttca ttgg                                     24

<210> SEQ ID NO 9
<211> LENGTH: 23
<212> TYPE: DNA
<213> ORGANISM: Artificial Sequence
```

```
<220> FEATURE:
<223> OTHER INFORMATION: primer sequence

<400> SEQUENCE: 9
gtgtcgattt cccacaaaca atg                                              23

<210> SEQ ID NO 10
<211> LENGTH: 23
<212> TYPE: DNA
<213> ORGANISM: Artificial Sequence
<220> FEATURE:
<223> OTHER INFORMATION: primer sequence

<400> SEQUENCE: 10
gttgattaag tccctgccct ttg                                              23

<210> SEQ ID NO 11
<211> LENGTH: 23
<212> TYPE: DNA
<213> ORGANISM: Artificial Sequence
<220> FEATURE:
<223> OTHER INFORMATION: primer sequence

<400> SEQUENCE: 11
tagtcaagtt cgaccgtctt ctc                                              23

<210> SEQ ID NO 12
<211> LENGTH: 23
<212> TYPE: DNA
<213> ORGANISM: Artificial Sequence
<220> FEATURE:
<223> OTHER INFORMATION: probe sequence

<400> SEQUENCE: 12
cacaccgccc gtcgctacta ccg                                              23

<210> SEQ ID NO 13
<211> LENGTH: 21
<212> TYPE: DNA
<213> ORGANISM: Artificial Sequence
<220> FEATURE:
<223> OTHER INFORMATION: primer sequence

<400> SEQUENCE: 13
ctccacaggt agctctagga g                                                21

<210> SEQ ID NO 14
<211> LENGTH: 23
<212> TYPE: DNA
<213> ORGANISM: Artificial Sequence
<220> FEATURE:
<223> OTHER INFORMATION: primer sequence

<400> SEQUENCE: 14
tctgaccaag atgttgatgt tgg                                              23

<210> SEQ ID NO 15
<211> LENGTH: 27
<212> TYPE: DNA
<213> ORGANISM: Artificial Sequence
<220> FEATURE:
<223> OTHER INFORMATION: probe sequence

<400> SEQUENCE: 15
tctctgctcc ccacctctaa gttgcca                                          27
```

```
<210> SEQ ID NO 16
<211> LENGTH: 21
<212> TYPE: DNA
<213> ORGANISM: Artificial Sequence
<220> FEATURE:
<223> OTHER INFORMATION: primer sequence

<400> SEQUENCE: 16
cggcagagta aaagagcaag c                                              21

<210> SEQ ID NO 17
<211> LENGTH: 24
<212> TYPE: DNA
<213> ORGANISM: Artificial Sequence
<220> FEATURE:
<223> OTHER INFORMATION: primer sequence

<400> SEQUENCE: 17
ggttgtagac aagttctcca aaac                                           24

<210> SEQ ID NO 18
<211> LENGTH: 21
<212> TYPE: RNA
<213> ORGANISM: Artificial Sequence
<220> FEATURE:
<223> OTHER INFORMATION: siRNA

<400> SEQUENCE: 18
ggugcccagu ucuccaagau u                                              21

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
ucuuggagaa cugggcaccu u                                              21

<210> SEQ ID NO 20
<211> LENGTH: 20
<212> TYPE: DNA
<213> ORGANISM: Artificial Sequence
<220> FEATURE:
<223> OTHER INFORMATION: primer sequence

<400> SEQUENCE: 20
ccccgcaaag acatcaaacc                                                20

<210> SEQ ID NO 21
<211> LENGTH: 23
<212> TYPE: DNA
<213> ORGANISM: Artificial Sequence
<220> FEATURE:
<223> OTHER INFORMATION: primer sequence

<400> SEQUENCE: 21
tgttgatgaa gtcatcgaca tcc                                            23
```